US009290461B2

(12) United States Patent
Zamir et al.

(10) Patent No.: US 9,290,461 B2
(45) Date of Patent: Mar. 22, 2016

(54) CRYSTALLINE MODIFICATIONS OF PROTHIOCONAZOLE

(75) Inventors: Sharona Zamir, Omer (IL); Doron Mason, Othniel (IL); Inna Faktorovitch, Beer Sheva (IL)

(73) Assignee: ADAMA MAKHTESHIM LTD (IL)

( * ) Notice: Subject to any disclaimer, the term of this patent is extended or adjusted under 35 U.S.C. 154(b) by 0 days.

(21) Appl. No.: 12/997,004

(22) PCT Filed: Jun. 17, 2009

(86) PCT No.: PCT/IL2009/000601
§ 371 (c)(1),
(2), (4) Date: Jan. 14, 2011

(87) PCT Pub. No.: WO2009/153785
PCT Pub. Date: Dec. 23, 2009

(65) Prior Publication Data
US 2011/0144172 A1 Jun. 16, 2011

Related U.S. Application Data

(60) Provisional application No. 61/073,058, filed on Jun. 17, 2008.

(51) Int. Cl.
*C07D 249/12* (2006.01)

(52) U.S. Cl.
CPC ................................ *C07D 249/12* (2013.01)

(58) Field of Classification Search
USPC ................... 424/45, 405; 514/384; 548/263.2
See application file for complete search history.

(56) References Cited

U.S. PATENT DOCUMENTS

| 5,789,430 | A | * | 8/1998 | Jautelat et al. ................ 514/384 |
| 5,859,039 | A | | 1/1999 | Jautelat |
| 7,176,226 | B2 | | 2/2007 | Seidel et al. |
| 2006/0106080 | A1 | | 5/2006 | Seidel et al. |
| 2007/0081947 | A1 | * | 4/2007 | Eble et al. ........................ 424/45 |

FOREIGN PATENT DOCUMENTS

| WO | WO96/16048 | | 5/1996 | |
| WO | WO 96/16048 | * | 5/1996 | ............ C07D 249/12 |

OTHER PUBLICATIONS

Braga, Dario and Grepioni, Fabrizia, "Making crystals from crystals: a green route to crystal engineering and polymorphism", Chem. Commun. p. 3635-3645, (2005).
Braga, Dario , et al., "Crystal Polymorphism and multiple crystal forms", Struct Bond, vol. 132, p. 25-50 (2009).
Braga, Dario and Grepioni, Fabrizia, Chapter 8: "Polymorphism, Crystal Transformations and Gas-Solid Reactions", Crystal Design: Structure and Function, vol. 7, p. 325-373 (2003).
Caira, Mino R., "Crystalline polymorphism of Organic Compounds", Topics in Current Chemistry, vol. 198, p. 163-208 (1998).
Laird, Trevor, "Polymorphism—Still Unpredictable", Organic Process Research & Development 2010, vol. 14, No. 1, p. 1 (Editorial), (2010).
Nangia, Ashwini and Desiraju, Gautam R., "Pseudopolymorphism: occurrences of hydrogen bonding organic solvents in molecular crystals", Chem. Commun., p. 605-606 (1999).
van Tonder, Elsa C., et al. "Preparation and Physicochemical Characterization of 5 Niclosamide Solvates and 1 Hemisolvate", AAPS PharmSciTech, vol. 5, No. 1, p. 1-10 (2004).
Desikan, Sridhar, et al., "Process Developement Challenges to Accommodate a Late-Appearing Stable Polymorph: A Case Study on the Polymorphism and Crystallization of a Fast-Track Drug Development Compound", Organic Process Research & Development, 2005, 9, 933-942.
Roy, Saikat and Matzger, Adam J., "Unmasking a Third Polymorph of a Benchmark Crystal-Structure-Prediction Coumpound", Angewandte Chemie Int. Ed., 2009, 48, 8505-8508.
International Search Report and Written Opinion mailed Jan. 13, 2010 for PCT/IL2009/000601, 16 pages.
Jautelat, M., et al., "Chemistry of Prothioconazole (JAU 6476)", Pflanzenschutz-Nachrichten Bayer 57/2004, 2, pp. 145-162.
Brittain, Harry G., "Preparation and Identification of Polymorphs and Solvatormorphs", Preformulation in Solid Dosage Form Development, 185-228 (5th Ed., M.C. Adeyey et al., eds.) 2008.
Brittain, Harry G. and Fiese, Eugene F., "Effects of Pharmaceutical Processing on Drug Polymorphs and Solvates" Harry G. Brittain, (ed.) in Polymorphism in Pharmaceutical Solids, Marcel Dekker, Inc., New York, 1999, 331-361.
Capes, Jacqueline S., "Contact Line Crystallization to Obtain Metastable Polymorphs", Crystal Growth & Design, vol. 7, 2007, 108-112.
Chemical Encyclopedic Dictionary, Moscow, The Soviet Encyclopedia Press, 1983, p. 130-131, with English translation.
Desikan, Sridhar, "Process Development Challenges to Accommodate a Late-Appearing Stable Polymorph: A Case Study on the Polymorphism and Crystallization of a Fast-Tract Drug Development Compount", Organic Process R&D, 2005, 9, 933-942.
Great Soviet Encyclopedia, Moscow, The Soviet Encyclopedia Press, 1976, v. 24, book 1, p. 164, with English translation.
Great Soviet Encyclopedia, Moscow, The Soviet Encyclopedia Press, 1970, v. 1, p. 535-536, with English translation.
Guillory, J. Keith, "Generation of Polymorphs, Hydrates, Solvates, and Amorphous Solids", in Polymorphism in Pharmaceuticals by Brittain, H.G., Chapter 5, p. 184-220 (1999).
Morissette, Sherry L., et al., "High-throughput crystallization: polymorphs, salts, co-crystals and solvates of pharmaceutical solids", Advanced Drug Delivery Reviews, 56, (2004) 275-300.
Roy and Matzger, "Unmasking a Third Polymorph of a Benchmark Crystal-Structure-Prediction Compound", Angewandte Chemie, 2009,048, 8505-8508.
Vippagunta, Sudha R., et al., "Crytalline Solids", Advanced Drug Delivery Reviews, 48, (2001) 3-26.
Hancock et al.; "Characteristics and Significance of the Amorphous State in Pharmaceutical Systems"; Journal of Pharmaceutical Sciences; vol. 86; No. 1; Jan. 1997; pp. 1-12.

(Continued)

*Primary Examiner* — Rebecca Anderson
*Assistant Examiner* — Po-Chih Chen
(74) *Attorney, Agent, or Firm* — Cantor Colburn LLP

(57) ABSTRACT

There is disclosed a crystalline DMSO solvate of prothioconazole as well as amorphous prothioconazole. Methods for making these solid forms, microbicidal compositions comprising them and uses thereof are also disclosed.

3 Claims, 5 Drawing Sheets

(56) References Cited

OTHER PUBLICATIONS

Anderton; "A Valuable Technique for Polymorph Screening"; American Pharmaceutical Review; Mar./Apr. 2007; pp. 34-40.
Lee et al.; "Crystal Polymorphism in Chemical Process Development"; Annu. Rev. Chem. Biomol. Eng.; 2011; 2; pp. 259-280.
Bates et al.; "Analysis of Amorphous and Nanocrystalline Solids from Their X-Ray Diffraction Patterns"; Pharmaceutical Research; vol. 23; No. 10; Oct. 2006; pp. 2333-2349.
Storey et al.; "Solid State Characterization of Pharmaceuticals"; Solid State Characterization of Pharmaceuticals, First Edition; Blackwell Publishing Ltd. ISBN: 978-1-405-13494-1; 2011; 170 pages.
Yu; "Amorphous pharmaceutical solids: preparation, characterization, and stabilization"; Advanced Drug Delivery Reviews; 48; 2001; pp. 27-42.
Aucamp et al. "Physicochemical Properties of Amorphous Roxithromycin Prepared by Quench Cooling of the Melt or Desolvation of a Chloroform Solvate" AAPS PharmSciTech, 2012, 13(2), pp. 467-476.
Gu, Chong-Hui et al. "Polymorph Screening: Influence of Solvents on the Rate of Solvent-Mediated Polymorphic Transformation" Journal of Pharmaceutical Sciences, 2001, 90(11), pp. 1878-1890.
Haleblian, John and McCrone, Walter "Pharmaceutical Applications of Polymorphism" Journal of Pharmaceutical Sciences, 1969, 58(8), pp. 911-929.
Jain, N.K. and Mohammedi, M.N. "Polymorphism in Pharmacy" Indian Drugs 1986, 23(6), pp. 315-329.
Liebenberg, Wilna "Crystal Polymorphism and its Occurrance Among Active Pharmaceutical Ingredients in South Africa" North-West University, South Africa, May 6, 2005, 29 pages.
Newman et al. "Solid-state analysis of the active pharmaceutical ingredient in drug products" Drug Discovery Today, vol. 8, No. 19, Oct. 2003, pp. 898-905.
O'Connor, Robert E. et al. "Powders" Remington: Practice of the Science and Pharmacy, 19th Ed. Chapter 91, Mack Publishing, Easton PA, 1995, pp. 1598-1614.
Papathoma, Sofia "Patenting Polymorphs at the European Patent Office", presentation—Barcelona, Spain, Jun. 19-21, 2006, pp. 1-14.
Radebaugh, Galen W. and Ravin, Louis J. "Preformulation", Remington: Practice of the Science and Pharmacy, 19th Ed. Chapter 83, Mack Publishing, Easton PA, 1995, pp. 1447-1462.
Rustichelli, C. et al. "Solid-state study of polymorphic drugs: carbamazepine" Journal of Pharmaceutical and Biomedial Analysis 2000, 23, pp. 41-54.
Schott, Hans "Colloidal Dispersions", Remington: Practice of the Science and Pharmacy, 19th Ed. Chapter 20, Mack Publishing, Easton PA, 1995, pp. 252-277.
Stahly, G. Patrick "Diversity in Single- and Multiple-Component Crystals. The Search for and Prevalence of Polymorphs and Cocrystals" Crystal Growth & Design, 2000, 7(6), pp. 1007-1026.

* cited by examiner

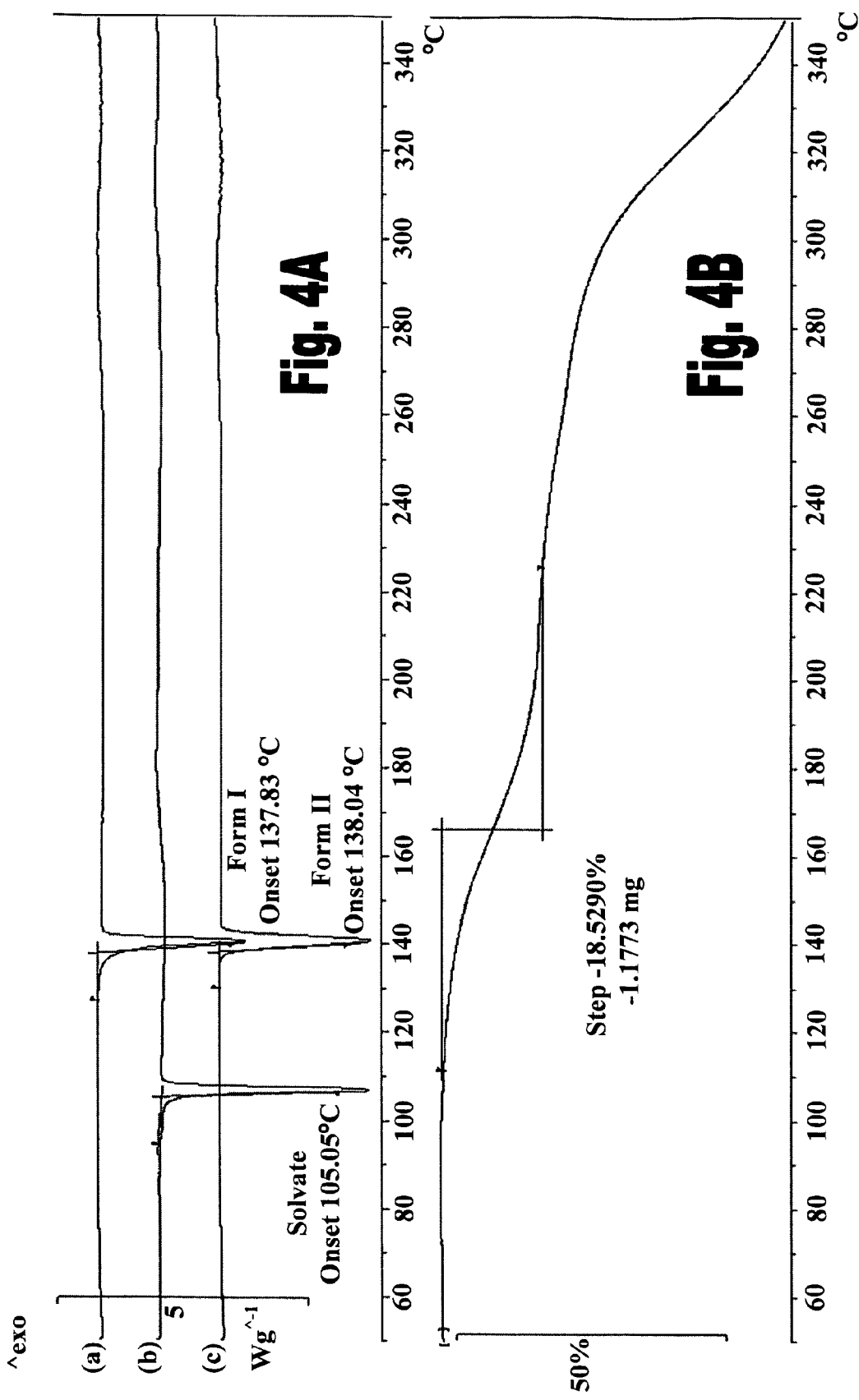

CRYSTALLINE MODIFICATIONS OF PROTHIOCONAZOLE

FIELD OF THE INVENTION

The invention relates to new solid forms of prothioconazole.

BACKGROUND OF THE INVENTION

Prothioconazole, 2-[(2RS)-2-(1-chlorocyclopropyl)-3-(2-chlorophenyl)-2-hydroxypropyl]-2H-1,2,4-triazole-3(4H)-thione, the structure of which is shown below, is used as a fungicide to treat infected crops. The molecule itself was first described in U.S. Pat. No. 5,789,430 and corresponding patent publications. Two crystalline forms of prothioconazole, named Form I and Form II, are disclosed in U.S. Pat. No. 5,789,430 and U.S. Patent Publication No. 2006/0106080, respectively. The contents of both of these U.S. patent publications are incorporated herein by reference. Form I is described in the '080 publication as being metastable at room temperature and Form II is described therein as being thermodynamically stable at room temperature.

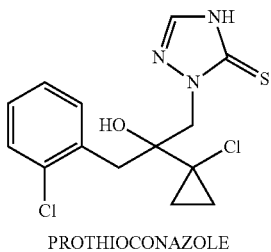 [SMILES: OC(Cc1ccccc1Cl)(Cn1nc[nH]c1=S)C1(Cl)CC1]

PROTHIOCONAZOLE

Prothioconazole structure is described in M. Jautelat et al., Pflanzenschultz-Nacbrichten Bayer, 57/2004, 2, 145-162.

Different crystalline forms of commercially important molecules, including amorphous forms and crystalline solvates, often possess different properties, which may be useful in different contexts. Thus, for example, crystalline forms are generally more stable than amorphous forms, making them useful for long-term storage of the solid material, whereas amorphous forms are often more readily soluble than crystalline forms and may thus be more useful for administration than crystalline forms for certain purposes.

The crystal form of a compound affects its physico-chemical properties, such as melting point, solubility, or dissolution rate. It is therefore advantageous that crystal forms with a range of lattice energies, and hence a range of physico-chemical properties be available, so as to allow for example the effectiveness of treatment (e.g. agricultural (such as plant treatment), veterinary or medicinal treatment) to be optimized. Thus for example a more stable, but less soluble form may be advantageous in some applications, whereas a higher energy, more soluble form may provide a different set of advantages in other applications.

Since prothioconazole is a microbicidal active agent, it is highly desirable to obtain new forms having improved solubility and/or dissolution rate.

Such new forms of prothioconazole may require lower dosage, reduce application rate, as compared to crystalline less soluble forms. Such new forms may have the particular advantages of inter alia having for example improved knock down effect as a result of the higher solubility and dissolution rate.

The amorphous form of solids is often characterized by a lower physical stability, sometimes accompanied by hygroscopic behavior, agglomeration, and other such changes. Additionally processing of amorphous powder is often difficult because of its instability. Much of this behaviour is a result of the normally small particle size, typically only a few microns. Therefore it will be advantageous to be able to influence the particle size of an amorphous material, in order to optimize it for different properties and applications. Further, it will be advantageous to obtain an amorphous form having relatively high particle size diameter.

Solid state chemistry of a crystal cannot predict whether an organic solvent can incorporate into the crystal. The manner in which solvation of a crystal may occur is also unpredictable. There are no rules that allow prediction of whether a compound will exist as solvated form of an organic solvent.

The discovery of new forms such as solvated form and amorphous form of for example an agriculturally, veterinary or medicinally useful compound may provide an opportunity to improve the performance characteristics of a product. It enlarges the repertoire of materials that a formulation scientist has available for designing, for example, a dosage form of a compound with a targeted release profile or other desired characteristic. It is clearly advantageous when this repertoire is enlarged by the discovery of new solvated crystalline forms or amorphous forms of a useful compound. Thus it will be advantageous to have new solvated crystalline forms or amorphous forms of prothioconazole, and efficient methods for their preparation.

SUMMARY OF THE INVENTION

The invention relates to a crystalline solvate of prothioconazole with dimethylsulfoxide (DMSO).

The invention additionally relates to a method for preparing a crystalline solvate of prothioconazole with DMSO comprising dissolving prothioconazole in DMSO; providing conditions suitable for crystallization of prothioconazole DMSO solvate; and isolating crystals of said solvate.

The invention further relates to a method for preparing amorphous prothioconazole, comprising heating crystalline prothioconazole until it melts, and cooling the melted prothioconazole, whereby to obtain amorphous prothioconazole.

The invention additionally relates to an amorphous form of prothioconazole.

The invention further relates to a microbicidal composition comprising crystalline prothioconazole DMSO solvate and one or more extenders and/or surfactants.

Moreover, the invention relates to a method for controlling unwanted microorganisms comprising applying an effective amount of crystalline prothioconazole DMSO solvate to one or both of the microorganisms and their habitat.

Additionally, the invention relates to a process for preparing a microbicidal composition comprising mixing crystalline prothioconazole DMSO solvate with one or more extenders and/or surfactants.

Further, the invention relates to a microbicidal composition comprising amorphous prothioconazole and one or more extenders and/or surfactants.

Still further, the invention relates to a method for controlling unwanted microorganisms comprising applying an effective amount of amorphous prothioconazole to one or both of the microorganisms and their habitat.

Moreover, the invention relates to a process for preparing a microbicidal composition comprising mixing amorphous prothioconazole with one or more extenders and/or surfactants.

Additionally, the invention relates to a microbicidal composition as herein above described for use in veterinary, medicine, or agriculture.

Further the invention relates to a method for controlling unwanted microorganism at a locus, said method comprising applying to said locus a microbicidally effective amount of a composition as described in the invention.

BRIEF DESCRIPTION OF THE DRAWINGS

FIG. 4A shows in overlayed form DSC plots for crystalline prothiconazole DMSO solvate, crystalline Form I and crystalline Form II prothioconazole. Plot (a) refers to Form I prothioconazole; Plot (b) refers to the prothiconazole DMSO solvate; Plot (c) refers to Form II prothioconazole.

FIG. 4B shows a TGA plot for crystalline prothioconazole DMSO solvate.

DETAILED DESCRIPTION OF THE INVENTION

Figure 1:
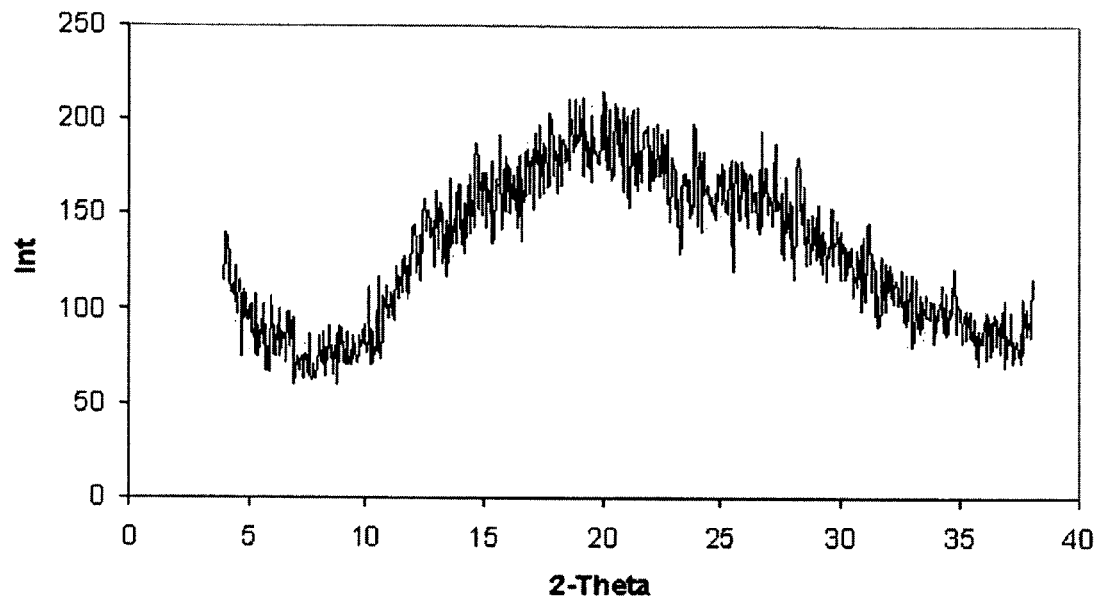
FIG. 1 shows a diffractogram of amorphous prothioconazole.

The invention relates to new solid forms of prothioconazole: crystalline prothioconazole DMSO solvate and an amorphous form of prothioconazole.

According to one aspect of the invention there is provided a crystalline solvate of prothioconozole with dimethylsulfoxide (DMSO).

As used herein the terms "crystalline solvate of prothioconozole", "crystalline solvate", "solvate", "prothioconazole solvate", "prothioconazole DMSO solvate", "crystalline prothioconazole DMSO solvate" and similar terms denote that a solvent molecule is contained within the crystalline lattice of the compound (i.e. prothioconazole). In this case the solvent refers to DMSO. These terms and similar terms may be used interchangeably in the present invention.

The "crystalline solvate" may be a crystalline solvate of the (−)-(S)-enantiomer, a crystalline solvate the (+)-(R)-enantiomer, a crystalline solvate of the racemate of said enantiomes, or any mixture of the crystalline solvate of said enantiomers (i.e. the (−)-(S)-enantiomer and (+)-(R)-enantiomer).

In some embodiments, the solvate is a 1:1 solvate.

As used herein the term "1:1 solvate" or the similar tem "monosolvate" denotes that the DMSO solvate with prothioconazole comprises approximately one DMSO molecule for each molecule of prothioconazole.

In the following description, DSC parameters (e.g. desolvation peak, desolvation onset, etc.) are provided for the prothioconozole DMSO solvate. It should be appreciated that, unless otherwise indicated, the accuracy of the temperature values, is +/−0.1° C. In some embodiments, the solvate is characterized by a desolvation peak in the range of 104.0° C.-109.0° C., as determined by differential scanning calorimetry (DSC).

According to a specific embodiment the solvate is characterized by a desolvation peak in the range 106-108° C.

According to a specific embodiment the desolvation peak is in the range 106.0-107.5° C.

According to a specific embodiment that desolvation peak is in the range 106.5-107.5° C.

According to certain embodiments the solvate is characterized by a desolvation peak in the range of 104.8° C.-106.4° C.+/−0.1° C.

According to certain embodiments the onset temperature of desolvation is in the range 104-106° C.

According to a specific embodiment the onset temperature of desolvation is in the range 104.5° C.-105.5° C.

According to a specific embodiment the onset temperature of desolvation is in the range 105-106° C.

According to a specific embodiment the differential scanning calorimetry (DSC) measurement is conducted at a scan rate of 5° C./min.

According to certain embodiments the enthalpy of desolvation of the monosolvate of prothioconazole is characterized by 95+/−5 J/g.

According to certain embodiments the prothioconazole DMSO solvate lacks a melting peak in the range of about 137° C. to about 145° C. According to a specific embodiment the prothioconazole solvate lacks a melting peak in the range of about 139° C. to about 145° C., and more specifically the prothioconazole solvate lacks a melting peak in the range of 139.1° C. to about 144.5° C.

A melting peak in said range is characteristic of crystalline prothioconazole form (e.g. form I and II). Without being bound to theory it is assumed that the desolvated form may dissolve in the released solvent or that the formed desolvated form may be in an amorphous form.

According to certain embodiments a broad flattened weak peak may appear following the desolvation peak.

In the following description, X-ray diffraction and FT-IR data are given for the prothioconozole solvate and the amorphous form. It should be appreciated that the accuracy of the diffraction angles (2θ values of peaks) is +/−0.2 degree (of 2θ) and the accuracy of the FT-IR absorption band values is +/−0.2 cm$^{-1}$.

In some embodiments, the solvate is characterized in that it has an FT-IR absorption spectrum having at least one absorption band selected from among the following values (expressed as cm$^{-1}$): (a) 712, (b) 859, (c), 1007 (d) 1401 and (e) 3259. In some embodiments, the value of the at least one absorption band is 712. In some embodiments, the value of the at least one absorption band is 859. In some embodiments, the value of the at least one absorption band is 1007. In some embodiments, the value of the at least one absorption band is 1401. In some embodiments, the value of the at least one absorption band is 3259. In some embodiments, the solvate is characterized in that it has at least two absorption bands selected from these values. In some embodiments, the values of the at least two absorption bands are 712 and 859. In some embodiments, the values of the at least two absorption bands are 712 and 1007. In some embodiments, the values of the at least two absorption bands are 712 and 1401. In some embodiments, the values of the at least two absorption bands are 712 and 3259. In some embodiments, the values of the at least two absorption bands are 859 and 1007. In some embodiments, the values of the at least two absorption bands are 859 and 1401. In some embodiments, the values of the at least two absorption bands are 859 and 3259. In some embodiments, the values of the at least two absorption bands are 1007 and 1401. In some embodiments, the values of the at least two absorption bands are 1007 and 3259. In some embodiments, the values of the at least two absorption bands are 1401 and 3259. In some embodiments, the solvate is characterized in that it has at least three absorption bands selected from these values. In some embodiments, the values of the at least three absorption bands are 712, 859 and 1007. In some embodiments, the values of the at least three absorption bands are 712, 859 and 1401. In some embodiments, the values of the at least three absorption bands are 712, 859 and 3259. In some embodiments, the values of the at least three absorption bands are 712, 1007 and 1401. In some embodiments, the values of the at least three absorption bands are 712, 1007 and 3259. In some embodiments, the values of the at least three absorption bands are 712, 1401 and 3259. In some embodiments, the values of the at least three absorption bands are 859, 1007 and 1401. In some embodiments, the values of the at least three absorption bands are 859, 1007 and 3259. In some embodiments, the values of the at least three absorption bands are 859, 1401 and 3259. In some embodiments, the values of the at least three absorption bands are 1007, 1401 and 3259. In some embodiments, the solvate is characterized in that it has at least four absorption bands selected from these values. In some embodiments, the values of the at least four absorption bands are 712, 859, 1007 and 1401. In some embodiments, the values of the at least four absorption bands are 712, 859, 1007 and 3259. In some embodiments, the values of the at least four absorption bands are 712, 859, 1401 and 3259. In some embodiments, the values of the at least four absorption bands are 712, 1007, 1401 and 3259. In some embodiments, the values of the at least four absorption bands are 859, 1007, 1401 and 3259. In some embodiments, the solvate is characterized in that it has all five of these absorption bands at these values. In some embodiments, the solvate is further characterized in that the FT-IR absorption of the solvate has one or more additional FT-IR absorption bands having a value selected from among the following (expressed as cm$^{-1}$): 644.6, 688.8, 781.5, 928.1, 1021.0, 1073.0, 1100.0, 1146.0, 1235.0, 1277.0, 1304.0, 1320.0, 1347.0, 1549.0 and 3137.0.

In some embodiments, the solvate is further characterized in that the FT-IR absorption of the solvate has one or more additional FT-IR absorption bands having a value selected from among the following (expressed as cm$^{-1}$): 644.6, 688.8, 781.5, 858.6, 928.1, 1021.0, 1073.0, 1100.0, 1146.0, 1235.0, 1262.0, 1277.0, 1293.0, 1304.0, 1320.0, 1347.0, 1443.0, 1549.0 and 3137.0.

It is appreciated that the term "one or more additional FT-IR absorption bands" covers individual bands and any combination thereof (i.e. one absorption band, two absorption bands, three absorption bands, four absorption bands, etc. (up to and including all bands) selected from the values recited above).

In a specific embodiment the FT-IR measurements are recorded at room temperature.

The term "room temperature" refers to 20-25° C.

Figure 2A:
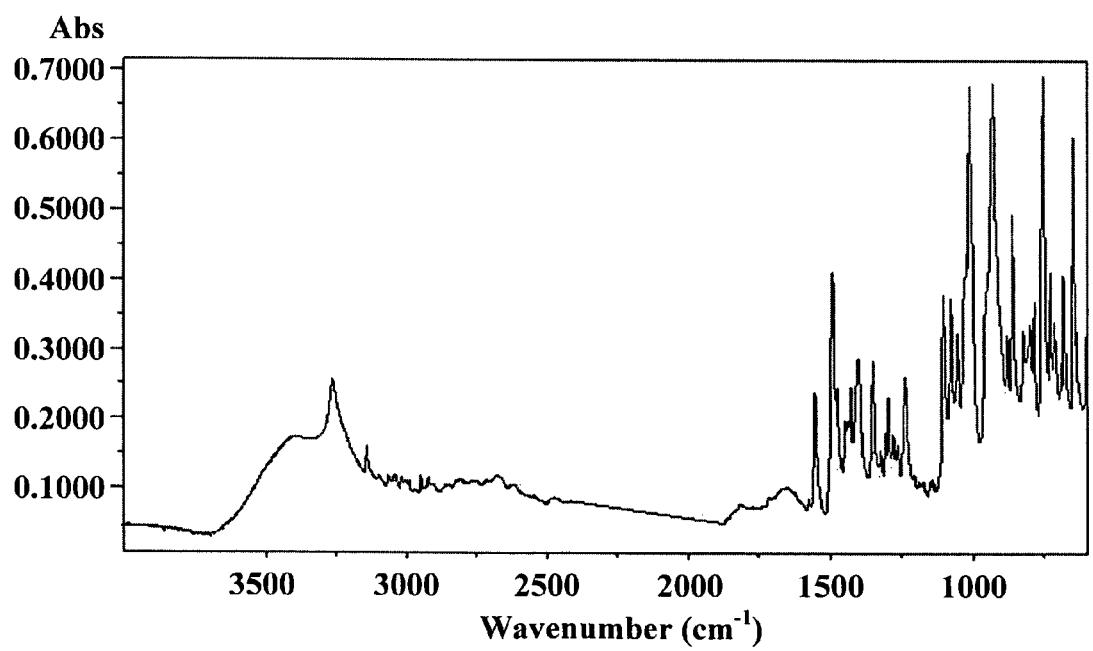
FIGS. 2A, 2B and 2C show FT-IR spectra of crystalline prothiconazole DMSO solvate, crystalline Form I and crystalline Form II prothioconazole, respectively.

According to a specific embodiment of the invention the solvate is characterized by having FT-IR absorption spectrum comprising bands essentially the same as shown in FIG. 2A.

In some embodiments, the solvate is characterized in that it has an X-ray powder diffraction (XRD) with at least one 2θ value selected from 7.5, 10.15, 15.45, 16.75, 22.75, 24.85, 31.35 and 34.6. In some embodiment, the at least one 2θ value is 7.5. In some embodiment, the at least one 2θ value is 10.15. In some embodiment, the at least one 2θ value is 15.45. In some embodiment, the at least one 2θ value is 16.75. In some embodiment, the at least one 2θ value is 22.75. In some embodiment, the at least one 2θ value is 24.85. In some embodiment, the at least one 2θ value is 31.35. In some embodiment, the at least one 2θ value is 34.6. In some embodiments, the solvate is characterized in that it has at least two of these 2θ values. In some embodiments, the at least two 2θ values are 7.5 and 10.15. In some embodiments, the at least two 2θ values are 7.5 and 15.45. In some embodiments, the at least two 2θ values are 7.5 and 16.75. In some embodiments, the at least two 2θ values are 7.5 and 22.75. In some embodiments, the at least two 2θ values are 7.5 and 24.85. In some embodiments, the at least two 2θ values are 7.5 and 31.35. In some embodiments, the at least two 2θ values are 7.5 and 34.6. In some embodiments, the at least two 2θ values are 10.15 and 15.45. In some embodiments, the at least two 2θ values are 10.15 and 16.75. In some embodiments, the at least two 2θ values are 10.15 and 22.75. In some embodiments, the at least two 2θ values are 10.15 and 24.85. In some embodiments, the at least two 2θ values are 10.15 and 31.35. In some embodiments, the at least two 2θ values are 10.15 and 34.6. In some embodiments, the at least two 2θ values are 15.45 and 16.75. In some embodiments, the at least two 2θ values are 15.45 and 22.75. In some embodiments, the at least two 2θ values are 15.45 and 24.85. In some embodiments, the at least two 2θ values are 15.45 and 31.35. In some embodiments, the at least two 2θ values are 15.45 and 34.6. In some embodiments, the at least two 2θ values are 16.75 and 22.75. In some embodiments, the at least two 2θ values are 16.75 and 24.85. In some embodiments, the at least two 2θ values are 16.75 and 31.35. In some embodiments, the at least two 2θ values are 16.75 and 34.6. In some embodiments, the at least two 2θ values are 22.75 and 24.85. In some embodiments, the at least two 2θ values are 22.75 and 31.35. In some embodiments, the at least two 2θ values are 22.75 and 34.6. In some embodiments, the at least two 2θ values are 24.85 and 31.35. In some embodiments, the at least two 2θ values are 24.85 and 34.6. In some embodiments, the at least two 2θ values are 31.35 and 34.6. In some embodiments, the solvate is characterized in that it has at least three of these 2θ values. In some embodiments, the at least three 2θ values are 7.5, 10.15 and 15.45. In some embodiments, the at least three 2θ values are 7.5, 10.15 and 16.75. In some embodiments, the at least three 2θ values are 7.5, 10.15 and 22.75. In some embodiments, the at least three 2θ values are 7.5, 10.15 and 24.85. In some embodiments, the at least three 2θ values are 7.5, 10.15 and 31.35. In some embodiments, the at least three 2θ values are 7.5, 10.15 and 34.6. In some embodiments, the at least three 2θ values are 7.5, 15.45 and 16.75. In some embodiments, the at least three 2θ values are 7.5, 15.45 and 22.75. In some embodiments, the at least three 2θ values are 7.5, 15.45 and 24.85. In some embodiments, the at least three 2θ values are 7.5, 15.45 and 31.35. In some embodiments, the at least three 2θ values are 7.5, 15.45 and 34.6. In some embodiments, the at least three 2θ values are 7.5, 16.75 and 22.75. In some embodiments, the at least three 2θ values are 7.5, 16.75 and 24.85. In some embodiments, the at least three 2θ values are 7.5, 16.75 and 31.35. In some embodiments, the at least three 2θ values are 7.5, 16.75 and 34.6. In some embodiments, the at least three 2θ values are 7.5, 22.75 and 24.85. In some embodiments, the at least three 2θ values are 7.5, 22.75 and 31.35. In some embodiments, the at least three 2θ values are 7.5, 22.75 and 34.6. In some embodiments, the at least three 2θ values are 7.5, 24.85 and 31.35. In some embodiments, the at least three 2θ values are 7.5, 24.85 and 34.6. In some embodiments, the at least three 2θ values are 7.5, 31.35 and 34.6. In some embodiments, the at least three 2θ values are 10.15, 15.45 and 16.75. In some embodiments, the at least three 2θ values are 10.15, 15.45 and 22.75. In some embodiments, the at least three 2θ values are 10.15, 15.45 and 24.85. In some embodiments, the at least three 2θ values are 10.15, 15.45 and 31.35. In some embodiments, the at least three 2θ values are 10.15, 15.45 and 34.6. In some embodiments, the at least three 2θ values are 10.15, 16.75 and 22.75. In some embodiments, the at least three 2θ values are 10.15, 16.75 and 24.85. In some embodiments, the at least three 2θ values are 10.15, 16.75 and 31.35. In some embodiments, the at least three 2θ values are 10.15, 16.75 and 34.6. In some embodiments, the at least three 2θ values are 10.15, 22.75 and 24.85. In some embodiments, the at least three 2θ values are 10.15, 22.75 and 31.35. In some embodiments, the at least three 2θ values are 10.15, 22.75 and 34.6. In some embodiments, the at least three 2θ values are 10.15, 24.85 and 31.35. In some embodiments, the at least three 2θ values are 10.15, 24.85 and 34.6. In some embodiments, the at least three 2θ values are 10.15, 31.35 and 34.6. In some embodiments, the at least three 2θ values are 15.45, 16.75 and 22.75. In some embodiments, the at least three 2θ values are 15.45, 16.75 and 24.85. In some embodiments, the at least three 2θ values are 15.45, 16.75 and 31.35. In some embodiments, the at least three 2θ values are 15.45, 16.75 and 34.6. In some embodiments, the at least three 2θ values are 15.45, 22.75 and 24.85. In some embodiments, the at least three 2θ values are 15.45, 22.75 and 31.35. In some embodiments, the at least three 2θ values are 15.45, 22.75 and 34.6. In some embodiments, the at least three 2θ values are 15.45, 24.85 and 31.35. In some embodiments, the at least three 2θ values are 15.45, 24.85 and 34.6. In some embodiments, the at least three 2θ values are 15.45, 31.35 and 34.6. In some embodiments, the at least three 2θ values are 16.75, 22.75 and 24.85. In some embodiments, the at least three 2θ values are 16.75, 22.75 and 31.35. In some embodiments, the at least three 2θ values are 16.75, 22.75 and 34.6. In some embodiments, the at least three 2θ values are 16.75, 24.85 and 31.35. In some embodiments, the at least three 2θ values are 16.75, 24.85 and 34.6. In some embodiments, the at least three 2θ values are 16.75, 31.35 and 34.6. In some embodiments, the at least three 2θ values are 22.75, 24.85 and 31.35. In some embodiments, the at least three 2θ values are 22.75, 24.85 and 34.6. In some embodiments, the at least three 2θ values are 22.75, 31.35 and 34.6. In some embodiments, the at least three 2θ values are 24.85, 31.35 and 34.6. In some embodiments, the solvate is characterized in that it has at least four of these 2θ values. In some embodiments, the at least four 2θ values are 7.5, 10.15, 15.45 and 16.75. In some embodiments, the at least four 2θ values are 7.5, 10.15, 15.45 and 22.75. In some embodiments, the at least four 2θ values are 7.5, 10.15, 15.45 and 24.85. In some embodiments, the at least four 2θ values are 7.5, 10.15, 15.45 and 31.35. In some embodiments, the at least four 2θ values are 7.5, 10.15, 15.45 and 34.6. In some embodiments, the at least four 2θ values are 7.5, 10.15, 16.75 and 22.75. In some embodiments, the at least four 2θ values are 7.5, 10.15, 16.75 and 24.85. In some embodiments, the at least four 2θ values are 7.5, 10.15, 16.75 and 31.35. In some embodiments, the at least four 2θ values are 7.5, 10.15, 16.75 and 34.6. In some embodiments, the at least four 2θ values are 7.5, 10.15, 22.75 and 24.85. In some embodiments, the at least four 2θ values are 7.5, 10.15, 22.75 and 31.35. In some embodiments, the at least four 2θ values are 7.5, 10.15, 22.75 and 34.6. In some embodiments, the at least four 2θ values are 7.5, 10.15, 24.85 and 31.35. In some embodiments, the at least four 2θ values are 7.5, 10.15, 24.85 and 34.6. In some embodiments, the at least four 2θ values are 7.5, 10.15, 31.35 and 34.6. In some embodiments, the at least four 2θ values are 7.5, 15.45, 16.75 and 22.75. In some embodiments, the at least four 2θ values are 7.5, 15.45, 16.75 and 24.85. In some embodiments, the at least four 2θ values are 7.5, 15.45, 16.75 and 31.35. In some embodiments, the at least four 2θ values are 7.5, 15.45, 16.75 and 34.6. In some embodiments, the at least four 2θ values are 7.5, 15.45, 22.75 and 24.85. In some embodiments, the at least four 2θ values are 7.5, 15.45, 22.75 and 31.35. In some embodiments, the at least four 2θ values are 7.5, 15.45, 22.75 and 34.6. In some embodiments, the at least four 2θ values are 7.5, 15.45, 24.85 and 31.35. In some embodiments, the at least four 2θ values are 7.5, 15.45, 24.85 and 34.6. In some embodiments, the at least four 2θ values are 7.5, 15.45, 31.35 and 34.6. In some embodiments, the at least four 2θ values are 7.5, 16.75, 22.75 and 24.85. In some embodiments, the at least four 2θ values are 7.5, 16.75, 22.75 and 31.35. In some embodiments, the at least four 2θ values are 7.5, 16.75, 22.75 and 34.6. In some embodiments, the at least four 2θ values are 7.5, 16.75, 24.85 and 31.35. In some embodiments, the at least four 2θ values are 7.5, 16.75, 24.85 and 34.6. In some embodiments, the at least four 2θ values are 7.5, 16.75, 31.35 and 34.6. In some embodiments, the at least four 2θ values are 7.5, 22.75, 24.85 and 31.35. In some embodiments, the at least four 2θ values are 7.5, 22.75, 24.85 and 34.6. In some embodiments, the at least four 2θ values are 7.5, 22.75, 31.35 and 34.6. In some embodiments, the at least four 2θ values are 7.5, 24.85, 31.35 and 34.6. In some embodiments, the at least four 2θ values are 10.15, 15.45, 16.75 and 22.75. In some embodiments, the at least four 2θ values are 10.15, 15.45, 16.75 and 24.85. In some embodiments, the at least four 2θ values are 10.15, 15.45, 16.75 and 31.35. In some embodiments, the at least four 2θ values are 10.15, 15.45, 16.75 and 34.6. In some embodiments, the at least four 2θ values are 10.15, 15.45, 22.75 and 24.85. In some embodiments, the at least four 2θ values are 10.15, 15.45, 22.75 and 31.35. In some embodiments, the at least four 2θ values are 10.15, 15.45, 22.75 and 34.6. In some embodiments, the at least four 2θ values are 10.15, 15.45, 24.85 and 31.35. In some embodiments, the at least four 2θ values are 10.15, 15.45, 24.85 and 34.6. In some embodiments, the at least four 2θ values are 10.15, 15.45, 31.35 and 34.6. In some embodiments, the at least four 2θ values are 10.15, 16.75, 22.75 and 24.85. In some embodiments, the at least four 2θ values are 10.15, 16.75, 22.75 and 31.35. In some embodiments, the at least four 2θ values are 10.15, 16.75, 22.75 and 34.6. In some embodiments, the at least four 2θ values are 10.15, 16.75, 24.85 and 31.35. In some embodiments, the at least four 2θ values are 10.15, 16.75, 24.85 and 34.6. In some embodiments, the at least four 2θ values are 10.15, 16.75, 31.35 and 34.6. In some embodiments, the at least four 2θ values are 10.15, 22.75, 24.85 and 31.35. In some embodiments, the at least four 2θ values are 10.15, 22.75, 24.85 and 34.6. In some embodiments, the at least four 2θ values are 10.15, 22.75, 31.35 and 34.6. In some embodiments, the at least four 2θ values are 10.15, 24.85, 31.35 and 34.6. In some embodiments, the at least four 2θ values are 15.45, 16.75, 22.75 and 24.85. In some embodiments, the at least four 2θ values are 15.45, 16.75, 22.75 and 31.35. In some embodiments, the at least four 2θ values are 15.45, 16.75, 22.75 and 34.6. In some embodiments, the at least four 2θ values are 15.45, 16.75, 24.85 and 31.35. In some embodiments, the at least four 2θ values are 15.45, 16.75, 24.85 and 34.6. In some embodiments, the at least four 2θ values are 15.45, 16.75, 31.35 and 34.6. In some embodiments, the at least four 2θ values are 15.45, 22.75, 24.85 and 31.35. In some embodiments, the at least four 2θ values are 15.45, 22.75, 24.85 and 34.6. In some embodiments, the at least four 2θ values are 15.45, 22.75, 31.35 and 34.6. In some embodiments, the at least four 2θ values are 15.45, 24.85, 31.35 and 34.6. In some embodiments, the at least four 2θ values are 16.75, 22.75, 24.85 and 31.35. In some embodiments, the at least four 2θ values are 16.75, 22.75, 24.85 and 34.6. In some embodiments, the at least four 2θ values are 16.75, 22.75, 31.35 and 34.6. In some embodiments, the at least four 2θ values are 16.75, 24.85, 31.35 and 34.6. In some embodiments, the at least four 2θ values are 22.75, 24.85, 31.35 and 34.6. In some embodiments, the solvate is characterized in that it has at least five of these 2θ values. In some embodiments, the at least five values are 7.5, 10.15, 15.45, 16.75 and 22.75. In some embodiments, the at least five values are 7.5, 10.15, 15.45, 16.75 and 24.85. In some embodiments, the at least five values are 7.5, 10.15, 15.45, 16.75 and 31.35. In some embodiments, the at least five values are 7.5, 10.15, 15.45, 16.75 and 34.6. In some embodiments, the at least five values are 7.5, 10.15, 15.45, 22.75 and 24.85. In some embodiments, the at least five values are 7.5, 10.15, 15.45, 22.75 and 31.35. In some embodiments, the at least five values are 7.5, 10.15, 15.45, 22.75 and 34.6. In some embodiments, the at least five values are 7.5, 10.15, 15.45, 24.85 and 31.35. In some embodiments, the at least five values are 7.5, 10.15, 15.45, 24.85 and 34.6. In some embodiments, the at least five values are 7.5, 10.15, 15.45, 31.35 and 34.6. In some embodiments, the at least five values are 7.5, 10.15, 16.75, 22.75 and 24.85. In some embodiments, the at least five values are 7.5, 10.15, 16.75, 22.75 and 31.35. In some embodiments, the at least five values are 7.5, 10.15, 16.75, 22.75 and 34.6. In some embodiments, the at least five values are 7.5, 10.15, 16.75, 24.85 and 31.35. In some embodiments, the at least five values are 7.5, 10.15, 16.75, 24.85 and 34.6. In some embodiments, the at least five values are 7.5, 10.15, 16.75, 31.35 and 34.6. In some embodiments, the at least five values are 7.5, 10.15, 22.75, 24.85 and 31.35. In some embodiments, the at least five values are 7.5, 10.15, 22.75, 24.85 and 34.6. In some embodiments, the at least five values are 7.5, 10.15, 22.75, 31.35 and 34.6. In some embodiments, the at least five values are 7.5, 10.15, 24.85, 31.35 and 34.6. In some embodiments, the at least five values are 7.5, 15.45, 16.75, 22.75 and 24.85. In some embodiments, the at least five values are 7.5, 15.45, 16.75, 22.75 and 31.35. In some embodiments, the at least five values are 7.5, 15.45, 16.75, 22.75 and 34.6. In some embodiments, the at least five values are 7.5, 15.45, 16.75, 24.85 and 31.35. In some embodiments, the at least five values are 7.5, 15.45, 16.75, 24.85 and 34.6. In some embodiments, the at least five values are 7.5, 15.45, 16.75, 31.35 and 34.6. In some embodiments, the at least five values are 7.5, 15.45, 22.75, 24.85 and 31.35. In some embodiments, the at least five values are 7.5, 15.45, 22.75, 24.85 and 34.6. In some embodiments, the at least five values are 7.5, 15.45, 22.75, 31.35 and 34.6. In some embodiments, the at least five values are 7.5, 15.45, 24.85, 3135 and 34.6. In some embodiments, the at least five values are 7.5, 16.75, 22.75, 24.85 and 31.35. In some embodiments, the at least five values are 7.5, 16.75, 22.75, 24.85 and 34.6. In some embodiments, the at least five values are 7.5, 16.75, 22.75, 31.35 and 34.6. In some embodiments, the at least five values are 7.5, 16.75, 24.85, 31.35 and 34.6. In some embodiments, the at least five values are 7.5, 22.75, 24.85, 31.35 and 34.6. In some embodiments, the at least five values are 10.15, 15.45, 16.75, 22.75 and 24.85. In some embodiments, the at least five values are 10.15, 15.45, 16.75, 22.75 and 31.35. In some embodiments, the at least five values are 10.15, 15.45, 16.75, 22.75 and 34.6. In some embodiments, the at least five values are 10.15, 15.45, 16.75, 24.85 and 31.35. In some embodiments, the at least five values are 10.15, 15.45, 16.75, 24.85 and 34.6. In some embodiments, the at least five values are 10.15, 15.45, 16.75, 31.35 and 34.6. In some embodiments, the at least five values are 10.15, 15.45, 22.75, 24.85 and 31.35. In some embodiments, the at least five values are 10.15, 15.45, 22.75, 24.85 and 34.6. In some embodiments, the at least five values are 10.15, 15.45, 22.75, 31.35 and 34.6. In some embodiments, the at least five values are 10.15, 15.45, 24.85, 31.35 and 34.6. In some embodiments, the at least five values are 10.15, 16.75, 22.75, 24.85 and 31.35. In some embodiments, the at least five values are 10.15, 16.75, 22.75, 24.85 and 34.6. In some embodiments, the at least five values are 10.15, 16.75, 22.75, 31.35 and 34.6. In some embodiments, the at least five values are 10.15, 16.75, 24.85, 31.35 and 34.6. In some embodiments, the at least five values are 10.15, 22.75, 24.85, 31.35 and 34.6. In some embodiments, the at least five values are 15.45, 16.75, 22.75, 24.85 and 31.35. In some embodiments, the at least five values are 15.45, 16.75, 22.75, 24.85 and 34.6. In some embodiments, the at least five values are 15.45, 16.75, 22.75, 31.35 and 34.6. In some embodiments, the at least five values are 15.45, 16.75, 24.85, 31.35 and 34.6. In some embodiments, the at least five values are 16.75, 22.75, 24.85, 31.35 and 34.6. In some embodiments, the solvate is characterized in that it has at least six of these 2θ values. In some embodiments, the at least six values are 7.5, 10.15, 15.45, 16.75, 22.75 and 24.85. In some embodiments, the at least six values are 7.5, 10.15, 15.45, 16.75, 22.75 and 31.35. In some embodiments, the at least six values are 7.5, 10.15, 15.45, 16.75, 22.75 and 34.6. In some embodiments, the at least six values are 7.5, 10.15, 15.45, 16.75, 24.85 and 31.35. In some embodiments, the at least six values are 7.5, 10.15, 15.45, 16.75, 24.85 and 34.6. In some embodiments, the at least six values are 7.5, 10.15, 15.45, 16.75, 31.35 and 34.6. In some embodiments, the at least six values are 7.5, 10.15, 15.45, 22.75, 24.85 and 31.35. In some embodiments, the at least six values are 7.5, 10.15, 15.45, 22.75, 24.85 and 34.6. In some embodiments, the at least six values are 7.5, 10.15, 15.45, 22.75, 31.35 and 34.6. In some embodiments, the at least six values are 7.5, 10.15, 15.45, 24.85, 31.35 and 34.6. In some embodiments, the at least six values are 7.5, 10.15, 16.75, 22.75, 24.85 and 31.35. In some embodiments, the at least six values are 7.5, 10.15, 16.75, 22.75, 24.85 and 34.6. In some embodiments, the at least six values are 7.5, 10.15, 16.75, 22.75, 31.35 and 34.6. In some embodiments, the at least six values are 7.5, 10.15, 16.75, 24.85, 31.35 and 34.6. In some embodiments, the at least six values are 7.5, 10.15, 22.75, 24.85, 31.35 and 34.6. In some embodiments, the at least six values are 7.5, 15.45, 16.75, 22.75, 24.85 and 31.35. In some embodiments, the at least six values are 7.5, 15.45, 16.75, 22.75, 24.85 and 34.6. In some embodiments, the at least six values are 7.5, 15.45, 16.75, 22.75, 31.35 and 34.6. In some embodiments, the at least six values are 7.5, 15.45, 16.75, 24.85, 31.35 and 34.6. In some embodiments, the at least six values are 7.5, 15.45, 22.75, 24.85, 31.35 and 34.6. In some embodiments, the at least six values are 7.5, 16.75, 22.75, 24.85, 31.35 and 34.6. In some embodiments, the at least six values are 10.15, 15.45, 16.75, 22.75, 24.85 and 31.35. In some embodiments, the at least six values are 10.15, 15.45, 16.75, 22.75, 24.85 and 34.6. In some embodiments, the at least six values are 10.15, 15.45, 16.75, 22.75, 31.35 and 34.6. In some embodiments, the at least six values are 10.15, 15.45, 16.75, 24.85, 31.35 and 34.6. In some embodiments, the at least six values are 10.15, 15.45, 22.75, 24.85, 31.35 and 34.6. In some embodiments, the at least six values are 10.15, 16.75, 22.75, 24.85, 31.35 and 34.6. In some embodiments, the at least six values are 15.45, 16.75, 22.75, 24.85, 31.35 and 34.6. In some embodiments, the solvate is characterized in that it has at least seven of these 2θ values. In some embodiments, the at least seven values are 7.5, 10.15, 15.45, 16.75, 22.75, 24.85 and 31.35. In some embodiments, the at least seven values are 7.5, 10.15, 15.45, 16.75, 22.75, 24.85 and 34.6. In some embodiments, the at least seven values are 7.5, 10.15, 15.45, 16.75, 22.75, 31.35 and 34.6. In some embodiments, the at least seven values are 7.5, 10.15, 15.45, 16.75, 24.85, 31.35 and 34.6. In some embodiments, the at least seven values are 7.5, 10.15, 15.45, 22.75, 24.85, 31.35 and 34.6. In some embodiments, the at least seven values are 7.5, 10.15, 16.75, 22.75, 24.85, 31.35 and 34.6. In some embodiments, the at least seven values are 7.5, 15.45, 16.75, 22.75, 24.85, 31.35 and 34.6. In some embodiments, the at least seven values are 10.15, 15.45, 16.75, 22.75, 24.85, 31.35 and 34.6. In some embodiments, the solvate is characterized in that it has all eight of these 2θ values. In some embodiments, the solvate is characterized in that it at least one additional 2θ value selected from the following: 15.95, 18.15, 19.40, 21.30, and 24.25.

In some embodiments, the solvate is characterized in that it at least one additional 2θ value selected from the following: 15.95, 18.15, 19.40, 20.30, 21.30, and 24.25. It is appreciated that the term "at least one additional 2θ value" covers individual 2θ values and any combination thereof (i.e. one 2θ value, two 2θ values, three 2θ values, four 2θ values, five 2θ values, or six 2θ values selected from the values recited above).

In a specific embodiment the X-ray powder diffraction is recorded using Cu-Kα radiation (wavelength equal to 1.54178 Å).

In a specific embodiment the X-ray powder diffraction is recorded at room temperature. The term "room temperature" refers to 20-25° C.

According to certain embodiments the DMSO solvate of prothioconazole is in substantially pure form.

As used herein, the term "substantially pure", when used in reference to a solvate of prothioconazole, refers to a DMSO solvate of prothioconazole which is equal or greater than about 90 weight % pure. This means that the DMSO solvate of prothioconazole does not contain more than about 10 weight % of any other compound and, in particular, does not contain more than about 10 weight % of any other form of prothioconazole. More preferably, the term "substantially pure" refers to a DMSO solvate of prothioconazole which is equal or greater than about 95 weight % pure. This means that the DMSO solvate of prothioconazole does not contain more than about 5 weight % of any other compound and, in particular, does not contain more than about 5 weight % of any other form of prothioconazole. Even more preferably, the term "substantially pure" refers to a DMSO solvate of prothioconazole which is equal or greater than about 97 weight % pure. This means that the DMSO solvate of prothioconazole does not contain more than about 3 weight % of any other compound and, in particular, does not contain more than about 3 weight % of any other form of prothioconazole.

In specific embodiments the term "substantially pure" includes a form of DMSO solvate of prothioconazole that is equal or greater than about 98%, 99%, 99.5%, or 99.8 weight % pure, and also including equal to about 100 weight % pure. According to certain embodiments the solvate of prothioconazole is characterized by having purity of equal or greater than about 85 weight %.

Figure 3A:
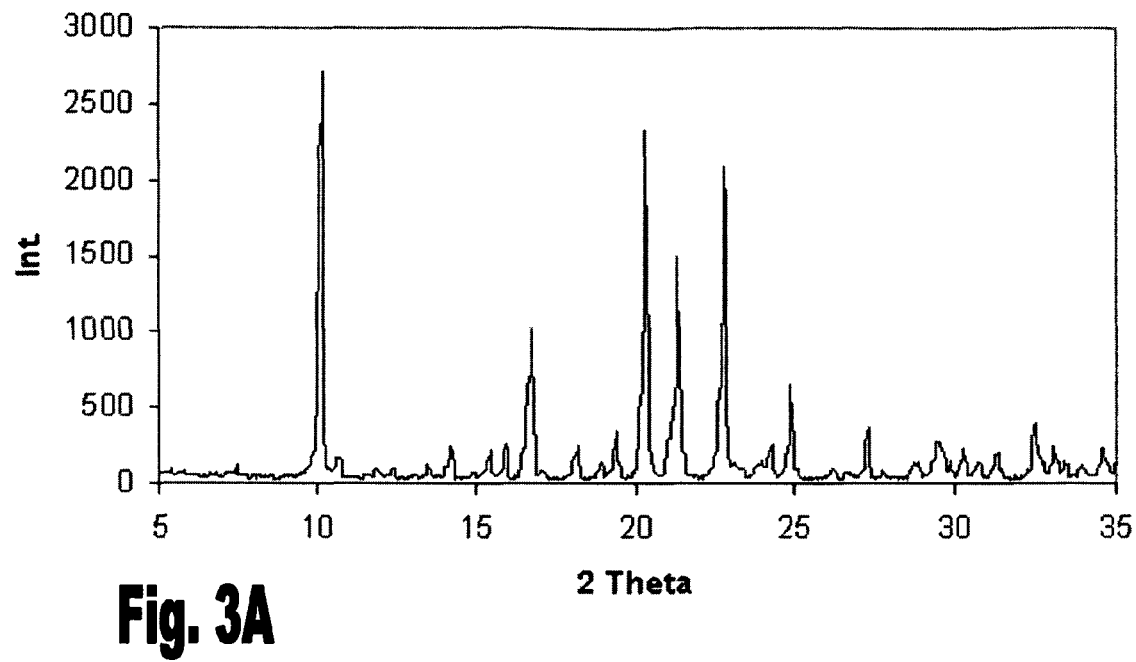
FIGS. 3A, 3B and 3C show respectively XRDs of crystalline prothiconazole DMSO solvate, crystalline Form I and crystalline Form II prothioconazole.

According to a specific embodiment of the invention the solvate is characterized by having an X-ray powder diffraction pattern essentially the same as shown in FIG. 3A.

According to a specific embodiment the solvate exhibits a TGA weight loss of about 18.5% (which corresponds to the monosolvate of DMSO).

According to a more specific embodiment the solvate exhibits a TGA weight loss of about 18.5% when heated up to about 230° C., As used herein by "about 18.5%" is meant 18.5%+/−0.5%, more specifically 18.5%+/−0.2%.

According to a specific embodiment the heating rate of the TGA measurements is conducted at a rate of 5° C./min.

It is appreciated that according to certain embodiments of the invention the TGA weight loss may vary according to the degree of purity of the DMSO solvate. For example a DMSO solvate having purity of 90% or higher may exhibit a TGA weight loss of 16.6-18.5%+/−0.5%.

There is provided according to an additional aspect of the invention a method for preparing a crystalline solvate of prothioconazole with DMSO comprising dissolving prothioconazole in DMSO; providing conditions suitable for crystallization of prothioconazole DMSO solvate; and isolating crystals of said solvate.

According to an embodiment of the invention said dissolving prothioconazole in DMSO is conducted with heating.

According to certain embodiments said conditions (i.e. conditions suitable for crystallization of prothioconazole DMSO solvate) are selected from cooling, adding an antisolvent (a secondary solvent), and a combination thereof.

According to an embodiment of the invention said conditions is cooling.

According to an embodiment of the invention the method comprising mixing prothioconazole and DMSO, heating the mixture, cooling the mixture, and isolating crystals of said solvate from the cooled mixture.

According to an embodiment of the invention the heating is conducted during or after said mixing.

In some embodiments the heating is conducted at a temperature of at least 50° C. In some embodiments the heating temperature is maintained for a period of time. In some embodiments the heating temperature is maintained for at least 30 minutes. One skilled in the art will readily determine the minimal conditions in his system that ensures complete dissolution. In some embodiments the cooling includes cooling the mixture to 40° C. or lower (i.e. the mixture obtained from dissolving prothioconazole in DMSO). In some embodiments the cooling includes cooling the mixture to 30-40° C. In some embodiments the cooling is conducted at a rate of about 0.5 to 2.0° C./min. In some embodiments the cooling is conducted at a rate of about ~1° C./min. In some embodiments one or more secondary solvents are added to the cooled mixture. In some embodiments one or more secondary solvents are added following cooling. The purpose of the secondary solvent is to act as an antisolvent. Thus the antisolvent (secondary solvent) is one in which prothioconazole has low solubility and therefore is able to act as an antisolvent. According to some embodiments the solubility of prothioconazole in the antisolvent (secondary solvent) is about 1 g/l or lower. In some embodiments the one or more secondary solvents are selected from cyclohexane and a combination of cyclohexane and water. In some embodiments, the mixture is further cooled. In some embodiments, the further cooling is to a temperature in the range of 5 to 15° C. In some embodiments, the further cooling is effected by placing the mixture (e.g. a vessel containing the mixture) in an environment which is at 0° C. or lower. According to a specific embodiment said environment is a bath. In some embodiments, the mixture is stirred as it is further cooled. In some embodiments, the isolating to includes filtering the crystals.

There is also provided according to an additional aspect of the invention a crystalline solvate of prothioconazole with DMSO obtainable by the method described herein.

There is also provided, in accordance with an additional aspect of the invention, a method for preparing amorphous prothioconazole, comprising heating crystalline prothioconazole until it melts, and then cooling the melted prothioconazole, whereby to obtain amorphous prothioconazole. In some embodiments, the cooling is effected by placing the melted prothioconazole (e.g. a vessel containing the melted prothioconazole) in an environment which is at 25° C. or lower. In some embodiments, the cooling is effected by placing the melted prothioconazole (e.g. a vessel containing the melted prothioconazole) in an environment which is at 20-25° C. In some embodiments, the cooling is effected by placing the melted prothioconazole (e.g. vessel containing the melted prothioconazole) in an environment which is at 0° C. or lower (for example in case rapid cooling is required or when working with high mass material which may require more drastic cooling methods). According to some embodiments said environment is a bath. In some embodiments, the bath is an ice-acetone bath. In some embodiments, the cooling is conducted at a cooling rate of 3-20° C./min, specifically, 4-20° C./min, more specifically 5-20° C./min, preferably 4-10° C./min, more preferably 5-10° C./min. In some embodiments cooling rate may be up 100° C./min (e.g. 2-100° C./min, 5-100° C./min, 20-100° C./min, 30-100° C./min, 50-100° C./min, or 75° C./min,). In some embodiments the cooling rate is higher than 100° C./min. In some embodiments the cooling rate is in the range 2-5000° C./min, more specifically 2-2000° C./min, even more specifically 2-1000° C./min.

It is appreciated that a more mild cooling rate (e.g. a cooling rate of 3-20° C./min, preferably 4-10° C./min, more preferably 5-10° C./min) will provide larger particles.

As used herein by "cooling rate of 3-20° C./min" is meant a cooling rate in the range 3 to 20° C./min. Similar used terms have equivalent meaning.

According to a specific embodiment the cooling rate is in 3-20° C./min and particle size diameter is as described in the present invention. According to a specific embodiment the particle size diameter d50 is in the range 20 to 200 micrometer.

There is also provided according to an additional aspect of the invention an amorphous form of prothioconazole obtainable by the methods described herein.

Surprisingly it has been observed that prothioconazole can be obtained in an amorphous form, even under relatively mild conditions of cooling (e.g. as described above, preferably about 4-10° C./min), thereby allowing a much larger particle size than is commonly expected for amorphous materials. Rapid cooling techniques may be employed to obtain amorphous prothioconazole of finer morphology.

According to a certain embodiments the cooling rate refers to an average cooling rate over the period of cooling.

According to some embodiments the cooling rate is controlled at a specific cooling rate value, or controlled at a cooling rate within a specific predetermined range.

There is also provided, according to a further aspect of the invention, an amorphous form of prothioconazole.

As used herein the term "amorphous" refers to a non-crystalline form of a compound. The amorphous form can be confirmed for example by conventional powder X-ray diffractometry. The amorphous form does not substantially exhibit any diffraction peaks. The amorphous form does not display a definitive X-ray diffraction pattern with sharp maxima.

According to a specific embodiment the amorphous prothioconazole is in substantially pure form.

As used herein, the term "substantially pure", when used in reference to amorphous prothioconazole, refers to amorphous prothioconazole which is equal or greater than about 90 weight % pure. This means that the amorphous prothioconazole does not contain more than about 10 weight % of any other compound and, in particular, does not contain more than about 10 weight % of any other form of prothioconazole. More preferably, the term "substantially pure", when used in reference to amorphous prothioconazole, refers to amorphous prothioconazole which is equal or greater than about 95 weight % pure. This means that the amorphous prothioconazole does not contain more than about 5 weight % of any other compound and, in particular, does not contain more than about 5 weight % of any other form of prothioconazole. Even more is preferably, the term "substantially pure", when used in reference to amorphous prothioconazole, refers to amorphous prothioconazole which is equal or greater than about 97 weight % pure. This means that the amorphous prothioconazole does not contain more than about 3 weight % of any other compound and, in particular, does not contain more than about 3 weight % of any other form of prothioconazole.

In specific embodiments the term "substantially pure" includes a form of amorphous prothioconazole that is equal or greater than about 98%, 99%, 99.5%, or 99.8 weight % pure and also including equal to about 100 weight % pure.

According to an embodiment of the invention, the X-ray diffraction pattern of the amorphous form is characterized by typical broad hump-peak from about 5 to about 40 (2θ), without any sharp peaks characteristic of a crystalline form. According to an embodiment of the invention the amorphous form is characterized by having an X-ray powder diffraction pattern essentially as shown in FIG. 1.

Referring to size of particles will be through their d50 meaning that 50% of the particles have the stated dimension or less (measured by volume). Thus, for examples, for particles stated to have a diameter of 20 micrometer ("microns"), this means that the particles have a d50 of 20 micrometer (d50=20 micrometer). The d50 may be measured by laser diffraction.

According to certain embodiments the amorphous prothioconazole is characterizes by having a particle size diameter d50 of 20 micrometer or above, d50 of 40 micrometer or above, d50 of 50 micrometer or above, d50 of 75 micrometer or above, d50 of 100 micrometer or above, d50 of 150 micrometer or above.

As used herein the term "d50 equal or above 20 micrometer" denotes that 50% of the particles have the stated diameter or less (i.e. less than a diameter value of 20 micrometer or above 20 micrometer). The other similar terms used have a similar meaning.

According to certain embodiments the amorphous prothioconazole is characterizes by having a particle size diameter, d50 in the range selected from 20 to 200 micrometer, 20 to 180 micrometer, 20 to 160 micrometer, 40 to 200 micrometer, 40 to 180 micrometer, 40 to 160 micrometer, 50 to 200 micrometer, 50 to 180 micrometer, 50 to 160 micrometer, 75 to 200 micrometer, 75 to 180 micrometer, 75 to 160 micrometer, 100 to 200 micrometer, 100 to 180 micrometer, 100 to 160 micrometer. According to a specific embodiment d50 is in the range 150 to 160 micrometer.

As used herein by the term "d50 in the range 20 to 200 micrometer" is meant
that 50% by volume of the particles have a diameter less than or equal to a value within the indicated range of 20 to 200 micrometer. Similarly the designation d50 in the range 20 to 180 micrometer means that 50% by volume of the particles have a diameter less than or equal to a value within the range of 20 to 180 micrometer. The other similar terms used have a similar meaning.

There is also provided, according to a further aspect of the invention a microbicidal composition comprising crystalline prothioconazole DMSO solvate and one or more extenders and/or surfactants.

As used herein by "one or more extenders and/or surfactants" is also meant an excipient selected from extenders, surfactants, and mixtures thereof.

As used here the term "microbicidal" (or "antimicrobial") is intended to encompass, but is not restricted to, all bactericidal and/or fungicidal activity.

As used herein, the terms "microbicidal", "antimicrobial activity" and similar terms refers to the ability of a compound to kill, inhibit or irreversibly prevent the growth of a microorganism.

The antimicrobial agent or microbicidal composition can be applied to an environment either presently exhibiting microbial growth (i.e., for therapeutic or curative treatment) or to an environment at risk of sustaining or supporting such growth (i.e., for prevention or prophylaxis).

According to a specific embodiment of the invention the microbicidal composition is useful for controlling unwanted microorganisms.

There is also provided, according to an additional aspect of the invention a method for controlling unwanted microorganisms comprising applying an effective amount of crystalline prothioconazole DMSO solvate to one or both of the microorganisms and their habitat.

The term "controlling" as used herein includes, but is not limited to, killing, inhibiting, or irreversibly preventing the growth of unwanted microorganisms, such as fungi and/or bacterial microorganisms.

According to an embodiment of the invention said unwanted microorganisms are selected from fungi and bacterial microorganisms. According to a specific embodiment the unwanted microorganisms is fungi.

The term "controlling" as used herein includes prophylactic use (e.g. to protect against infection, pest (e.g. fungi) infestation, etc.) and curative use (i.e. to eradicate infection, pest (e.g. fungi) infestation etc.).

The term "effective amount" or similar terms used herein mean the amount of a to compound of the present invention that kills, inhibits, or irreversibly prevents, the propagation and/or growth of unwanted microorganisms (e.g. a bacterial or fungal species) relative to an untreated control.

As understood by context the terms "compound", "active ingredient", "active agent", "antimicrobial agent", and similar terms used, refer to prothioconazole DMSO solvate or the amorphous form of prothioconazole.

According to certain embodiments said controlling unwanted microorganisms excludes controlling of unwanted microorganisms in a human body.

According to certain embodiments said controlling unwanted microorganisms excludes controlling of unwanted organisms in a human or animal body.

According to certain embodiments said controlling unwanted microorganisms excludes treating a human body.

According to certain embodiments said controlling unwanted microorganisms excludes treating a human or animal body.

There is also provided, according to an additional aspect of the invention, a process for preparing microbicidal compositions comprising mixing crystalline prothioconazole DMSO solvate with one or more extenders and/or surfactants.

There is also provided, according to an additional aspect of the invention, a microbicidal composition comprising amorphous prothioconazole and one or more extenders and/or surfactants.

There is also provided, according to an additional aspect of the invention, a method for controlling unwanted microorganisms comprising applying an effective amount of amorphous prothioconazole to one or both of the microorganisms and their habitat.

There is also provided, according to an additional aspect of the invention, a process for preparing microbicidal compositions comprising mixing amorphous prothioconazole with one or more extenders and/or surfactants.

There is also provided, according to an additional aspect of the invention, a microbicidal composition as described in the invention for use in veterinary, medicine, or agriculture. The agricultural use may be for example for treating fields or crops.

There is also provided, according to an additional aspect of the invention, a method for controlling unwanted microorganism at a locus, said method comprising applying to said locus a microbicidally effective amount of a composition as described in the invention.

According to an embodiment of the invention said locus is selected from plant, plant parts, soil, and industrial material, Prothioconazole per se, as crystalline Form I, may be prepared in accordance with known procedures, as described e.g. in U.S. Pat. No. 5,789,430. Crystalline Form II prothioconazole may be prepared as described in U.S. Patent Publication No. 20060106080.

The solid forms of prothioconazole disclosed herein, viz. crystalline prothioconazole DMSO solvate and amorphous prothioconazole, are each suitable for preparing formulations. With regard to the crystalline solvate, this is so even if, following preparation of the formulation, the active compound is no longer present in crystalline form but in solution. It is particularly advantageous that the solid forms of prothioconazole disclosed herein are in each case converted quantitatively into the desired formulation. This reduces the risk of inaccurate dosage owing to agglomerization and/or sedimentation. The solid forms of prothioconazole disclosed herein can exhibit excellent microbicidal action and can be employed for controlling to unwanted microorganisms, such as fungi and bacteria, in crop protection and in the protection of materials.

The solid forms of prothioconazole disclosed herein can be used to treat plants and parts of plants. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

Treatment of the plants and parts of plants with a solid form of prothioconazole disclosed herein is carried out directly or by action on their surroundings, habitat or storage space by the customary treatment methods, for example by immersion, spraying, evaporating, fogging, scattering, painting on and, in the case of propagation material, in particular in the case of seeds, also by applying one or more coats.

In the protection of materials, a solid form of prothioconazole disclosed herein can be employed for protecting industrial materials against infection with, and destruction by, unwanted microorganisms.

For the treatment of plants and parts of plants, in general amounts of active ingredient (a.i.) per ha from about 10 g/ha to about 3000 g/ha, more specifically from about 50 to about 1000 g/ha, even more specifically from about 150 to about 750 g/ha may be used.

For the treatment of seeds, in general amounts of the active ingredient from about 0.001 to about 20 g per kilogram of seed may be used, more specifically from about 0.01 to about 5 g per kilogram of seed, even more specifically from about 0.02 to about 0.5 g per kilogram of seed may be used.

The optimum amount employed can be determined for the use in each case by series of tests. The amount may vary depending on the specific plant, material to be treated, type of microorganism, degree of infestation, and other factors. It is well within an ordinary skill in the art to determine the necessary amount of the active ingredient.

The solid forms of prothioconazole disclosed herein can be converted to formulations known in the art, such as solutions, emulsions, suspensions, powders, foams, pastes, granules, aerosols and microencapsulations in polymeric substances and in coating compositions for seeds, and ULV cool and warm fogging formulations. These formulations may be produced in a known manner, for example by mixing the solid form of prothioconazole with extenders (auxiliaries suitable for the preparation of the formulation), such as liquid solvents, liquefied gases under pressure, and/or solid carriers, optionally with the use of surfactants, that is emulsifiers and/or dispersants and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or water. Liquefied gaseous extenders or carriers are to be understood as meaning liquids which are gaseous at standard temperature and under atmospheric pressure, for example aerosol propellants such as halogenated hydrocarbons, or butane, propane, nitrogen and carbon dioxide. Suitable solid carriers are, for example, ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are, for example, crushed and fractionated natural rocks such as calcite, marble, pumice, sepiolite and dolomite, or synthetic granules of inorganic and organic materials, and granules of organic material such as sawdust, coconut shells, maize cobs and tobacco stalks. Suitable emulsifiers and/or foam formers are, for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or protein hydrolysates. Suitable dispersants are, for example, lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations (compositions) generally comprise between about 0.01 and about 99 percent by weight of crystalline prothioconazole DMSO solvate or amorphous prothioconazole or more specifically between about 0.1 and about 95 percent by weight of crystalline prothioconazole DMSO solvate or amorphous prothioconazole, preferably between about 0.5 and about 90% wt of crystalline prothioconazole DMSO solvate or amorphous prothioconazole.

According to certain embodiments the new solid forms of prothioconazole disclosed herein may be used in mixture with other prothioconazole forms. According to some embodiments prothioconazole DMSO solvate may be used in combination with other priothioconazole forms (e.g. a priothioconazole form selected from amorphous priothioconazole, prohioconazole form I, prothioconazole form II, and a mixture thereof). According to some embodiments amorphous prothioconazole may be used in combination with other priothioconazole forms (e.g. a priothioconazole form selected from priothioconazole DMSO solvate, prohioconazole form I, prothioconazole form II, and a mixture thereof).

The solid forms of prothioconazole disclosed herein can be used as such or in formulations, also in a mixture with at least one known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components. Examples of suitable mixing components are the following compounds:

Fungicides: aldimorph, ampropylfos, ampropylfos potassium, andoprim, anilazine, azaconazole, azoxystrobin, benalaxyl, benodanil, benomyl, benzamacril, benzamacril-isobutyli bialaphos, binapacryl, biphenyl, bitertanol, blasticidin-S, bromuconazole, bupirimate, buthiobate, calcium polysulphide, carpropamid, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenhexamid, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, fluoxastrobin, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, iprovalicarb, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, picoxystrobin, pimaricin, piperalin, polyoxin, polyoxorim, probenazole, prochloraz, procymidone, propamocarb, propanosine-sodium, propiconazole, propineb, pyraclostrobin, pyrazophos, pyrifenox, pyrimethanil, pyroquilon, pyroxyfur, quinconazole, quintozene (PCMB), quinoxyfen sulphur and sulphur preparations, spiroxamine tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, trifloxystrobin, triflumizole, triforine, triticonazole, uniconazole, validamycin A, vinclozolin, viniconazole, zarilamide, zineb, ziran and alo Dagger G, OK-8705, OK-8801, α-(1,1-dimethylethyl)-β-(2-phenoxyethyl)-1H-1,2,4-triazole-1-ethanol, α-(2,4-dichlorophenyl)-β-fluoro-α-propyl-1H-1,2,4-triazole-1-ethanol, α-(2,4-dichlorophenyl)-β-methoxy-β-methyl-1H-1,2,4-triazole-1-ethanol, α-(5-methyl-1,3-dioxan-5-yl)-β-[[4-(trifluoromethyl)phenyl]methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyiino)-N-methyl-2-phenoxyphenylacetamide, 1-(2,4-dichlorophenyl)-2-(1H-1,2,4-triazol-1-yl)ethanone O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)sulphonyl]-4-methylbenzene, 1-[[2-(2,4-dichlorophenyl)-1,3-dioxolan-2-yl]methyl]-1H-imidazole, 1-[[2-(4-chlorophenyl)-3-phenyloxiranyl]methyl]-1H-1,2,4-triazole, 1-[1-[2-[(2,4-dichlorophenyl)methoxy]phenyl]ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,6-dichloro-5-(methylthio)-4-pyrimidinylthiocyanate, 2,6-dichloro-N-(4-trifluoromethylbenzyl)benzamide, 2,6-dichloro-N-[[4-(trifluoromethyl)phenyl]methyl]benzamide, 2-(2,3,3-triiodo-2-propenyl)-2H-tetrazole, 2-[(1-methylethyl)sulphonyl]-5-(trichloromethyl)-1,3,4-thiadiazole, 2-[[6-deoxy-4-O-(4-O-methyl-β-D-glycopyranosyl)-α-D-glucopyranosyl]amino]-4-methoxy-1H-pyrrolo[2,3-d]pyrimidine-5-carbonitrile, 2-aminobutane, 2-bromo-2-(bromomethyl)pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)acetamide, 2-phenylphenol (OPP), 3,4-dichloro-1-[4-(difluoromethoxy)phenyl]-1H-pyrrole-2,5-dione, 3,5-dichloro-N-[cyano[(1-methyl-2-propynyl)oxy]methyl]benzamide, 3-(1,1-dimethylpropyl)-1-oxo-1H-indene-2-carbonitrile, 3-[2-(4-chlorophenyl)-5-ethoxy-3-isoxazolidinyl]pyridine, 4-chloro-2-cyano-N,N-dimethyl-5-(4-methylphenyl)-1H-imidazole-1-sulphonamide, 4-methyltetrazolo[1,5-a]quinazolin-5(4H)-one, 8-hydroxyquinoline sulphate, 9H-xanthene-2-[(phenylamino)carbonyl]-9-carboxylic hydrazide, bis(1-methylethyl)-3-methyl-4-[(3-methylbenzoyl)oxy]-2,5-thiophenedicarboxylate, cis-1-(4-chlorophenyl)-2-(1H-1,2,4-triazol-1-yl)cycloheptanol, cis-4-[3-[4-(1,1-dimethylpropyl)phenyl-2-methylpropyl]-2,6-dimethylmorpholine hydrochloride, ethyl [(4-chlorophenyl)azo]cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,6-dimethylphenyl)-2-methoxy-N-(tetrahydro-2-oxo-3-furanyl)acetamide, N-(2,6-dimethylphenyl)-2-methoxy-N-(tetrahydro-2-oxo-3-thienyl)acetamide, N-(2-chloro-4-nitrophenyl)-4-methyl-3-nitrobenzenesulphonamide, N-(4-cyclohexylphenyl)-1,4,5,6-tetrahydro-2-pyrimidine amine, N-(4-hexylphenyl)-1,4,5,6-tetrahydro-2-pyrimidineamine, N-(5-chloro-2-methylphenyl)-2-methoxy-N-(2-oxo-3-oxazolidinyl)acetamide, N-(6-methoxy-3-pyridinyl)cyclopropanecarboxamide, N-[2,2,2-trichloro-1-[(chloroacetyl)amino]ethyl]benzamide, N-[3-chloro-4,5-bis(2-propinyloxy)phenyl]-N'-methoxymethanimidamide, N-formyl-N-hydroxy-DL-alaninesodium salt, O,O-diethyl-[2-(dipropylamino)-2-oxoethyl]ethylphosphoramidothioate, O-methyl-5-phenyl phenylpropylphosphoramidothioate, S-methyl-1,2,3-benzothiadiazole-7-carbothioate, spiro[2H]-1-benzopyrane-2,1'(3'H)-isobenzofuran]-3'-one, 4-[(3,4-dimethoxyphenyl)-3-(4-fluorophenyl)acryloyl]morpholine.

Bactericides: bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/acaricides/nematicides: abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin, *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, bistrifluoron, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, to chlorfenapyr, chlorfenvinphos, chlorfluazuron, chlormephos, chlorpyrifos, chlorpyrifos M, chlovaphorthrin, chromafenozide, cis-resmethrin, cispermethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, dicofol, diflubenzuron, dimethoat, dimethylvinphos; diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flumethrin, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, indoxacarb, isazofos, isofenphos, isoxathion, ivermectin, nuclear polyhedrosis viruses, lambda-cyhalothrin, lufenuron, malathion, mecarbam, metaldehyde, methamidophos, *Metharhizium anisopliae, Metharhizium flavoviride*, methidathion, methiocarb, methoprene, methomyl, methoxyfenozide, metolcarb, metoxadiazone, mevinphos, milbemectin, milbemycin, monocrotophos, naled, nitenpyram, nithiazine, novaluron, ometothoate, oxamyl, oxydemethon M, Paecilomyces fumosoroseus, parathion A, parathion M, permethrin, phenthoate, phorat, phosalone, phosmet, phosphamidon, phoxim, pirimicarb, pirimiphos A, piriniphos M, profenofos, promecarb, propargite, propoxur, prothiofos, prothoat, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, spirodiclofen, sulfotep, sulprofos, tau-fluvalinate, tebufenozide, tebufenpyrad, tebupirimiphos, teflubenzuron, tefluthrin, temephos, temivinphos, terbufos, tetrachlorvinphos, tetradifon, theta-cypermethrin, thiacloprid, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii*, YI 5302, zeta-cypermethrin, zolaprofos, (1R-cis)[5-(phenylmethyl)-3-furanyl]methyl 3-[(dihydro-2-oxo-3(2H)-furanylidene)methyl]-2,2-dimethylcyclopropanecarboxylate, (3-phenoxyphenyl)methyl-2,2,3,3-tetramethylcyclopropanecarboxylate, 1-[(2-chloro-5-thiazoly])methyl)tetrahydro-3,5-dimethyl-N-nitro-1,3,5-tri-azine-2(1H)-imine, 2-(2-chloro-6-fluorophenyl)-4-[4-(1,1-dimethylethyl)phenyl]-4,5-dihydrooxazole, 2-(acetyloxy)-3-dodecyl-1,4-naphthalenedione, 2-chloro-N-[[[4-(1-phenylethoxy)phenyl]amino]carbonyl]benzamide, 2-chloro-N-[[[4-(2,2-dichloro-1,1-difluoroethoxy)phenyl]amino]carbonyl]benzamide, 3-methylphenyl propylcarbamate, 4-[4-(4-ethoxyphenyl)-4-methylpentyl]-1-fluoro-2-phenoxybenzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone, *Bacillus thuringiensis* strain EG-2348, [2-benzoyl-1-(1,1-dimethylethyl)hydrazinobenzoic acid, 2,2-dimethyl-3-(2,4-dichlorophenyl)-2-oxo-1-oxaspiro[4.5] dec-3-en4-yl butanoate, [3-[(6-chloro-3-pyridinyl)methyl]-2-thiazolidinylidene]cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]carbamate, N-(3,4,4-trifluoro-1-oxo-3-butenyl)glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]ethylphosphoramidothioate, N-cyanomethyl-4-trifluoromethylnicotinamide, 3,5-dichloro-1-(3,3-dichloro-2-propenyloxy)-4-[3-(5-trifluoromethylpyridin-2-yloxy)propoxy]benzene.

A mixture with other known active compounds, such as herbicides, or with fertilizers and growth regulators, is also possible.

In addition, the crystalline prothioconazole DMSO solvate and amorphous prothioconazole also have very good antimycotic activity (antifungal activity). They have a very broad antimycotic activity spectrum in particular against dermatophytes and yeasts, moulds and diphasic fungi (for example *Candida* species such as *Candida albicans, Candida glabrata*) and also *Epidermophyton floccosum, Aspergillus* species such as *Aspergillus niger* and *Aspergillus fumigatus, Trichophyton* species such as *Trichophyton mentagrophytes, Microsporon* species such as *Microsporon canis* and *audouinii*. The list of these fungi by no means limits the mycotic spectrum covered, but is only for illustration.

The crystalline prothioconazole DMSO solvate or amorphous prothioconazole can be used as such, in the form of its formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compound by the ultra-low volume method, or to inject the active compound preparation or the active compound itself into the soil. It is also possible to treat the seeds of the plants.

As already mentioned above, the crystalline prothioconazole DMSO solvate or amorphous prothioconazole can be used to treat all plants and parts thereof. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated. Plant cultivars are understood as meaning plants with novel properties ("traits") which have been grown by conventional cultivation, by mutagenesis or by recombinant DNA techniques. These may be cultivars, biotypes or genotypes.

Depending on the plant species or plant cultivars, their location and growth conditions (soils, climate, vegetation period, diet), the treatment may also result in superadditive ("synergistic") effects. Thus, for example, reduced application rates and/or a widening of the activity spectrum and/or an increase in the activity of the substance to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferably to be treated include all plants which, in the genetic modification, received genetic material which imparts particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defense of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis—is given to maize, soya beans, potatoes, cotton and oilseed rape. Traits that are emphasized are in particular increased defense of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits which are also particularly emphasized are the increased resistance of plants to fungi, bacteria and viruses by systemic acquired resistance (SAR), systemin, phytoalexins, elicitors and resistance genes and the correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned also include the varieties sold under the name Clearfield® (for example maize). Of course, these statements also apply to plant cultivars having these genetic traits or genetic traits still to be developed, which cultivars will be developed and/or marketed in the future.

The plants listed can be treated in a particularly advantageous manner with the crystalline prothioconazole DMSO solvate or amorphous prothioconazole or mixtures containing one or both of them.

The preparation of crystalline prothioconazole DMSO solvate and amorphous prothioconazole is illustrated by the examples below.

EXAMPLES

Analytical Methods

DSC was measured using a Differential Scanning calorimeter from Mettler Toledo equipped with an $821^e$ module. Thermogravimetric analysis was measured using a thermogravimetric analyser from Mettler Toledo equipped with an $851^e$ module. Samples of 2-4 mg (DSC) or 4-6 mg (TGA) each were purged with nitrogen flow (80 ml/min) during the measurements, which were recorded using a scan rate of 5° C./min. Scan range was 50-350° C. Aluminium standard crucibles of 40 µL with hole were used. Evaluation of the results was performed using $STAR^e$ software from Mettler-Toledo.

IR spectra were measured using a ReactIR™ 1000 Fourier transform infrared (FT-IR) spectrophotometer ReactIR™ from Applied Systems (ATR method, MCT detector), equipped with a diamond window. Samples for IR were held in a DuraSamplIR™ sampling device. The diamond sensor had a standard ZnSe focusing optic. The powdered samples were compressed in the sampling device and were measured with a resolution of 4 $cm^{-1}$ using 256 scans.

X-Ray powder diffraction data were collected on a Philips PW 1050/70 powder diffractometer operated at 40 kV and 30 mA using $CuK_\alpha$ radiation (wavelength equal to 1.54178 Å) and a diffracted beam graphite monochromator. The typical 0-2θ scan range was 3-35° 2θ with a step size of 0.05° and a count time of 0.5 seconds per step. Samples were ground prior to measurement using an agate mortar and pestle. The powder obtained was then pressed into an aluminum sample holder having a rectangular cavity of dimensions 20 min×15 mm×0.5 mm.

Example 1

Preparation of Amorphous Prothioconazole

Example 1A

Crystalline Form I prothioconazole (1 g) was heated in a 20 ml beaker over a heating plate until the sample melted. The molten material was maintained at elevated temperature (~140° C.) for a further 10 minutes and then immediately placed in an ice-acetone bath (–13° C.) for rapid cooling. The glass-like solid was analyzed by X-ray powder diffraction. The obtained diffractogram exhibited no distinct peaks and was thus determined to be amorphous. FIG. 1 shows a diffractogram of amorphous prothioconazole.

The conversion from amorphous form to form I measured by DSC gave a broad peak with an onset at 75-80° C. (The peak maximum depended strongly on the rate of heating.).

Example 1B

Example 1A was repeated with the following modifications: prothioconazole was completely melted in an open porcelain dish with heating. The melt was removed from the heat source and allowed to cool to room temperature to obtain an amorphous prothioconazole. The average cooling rate was approximately 4-5° C./min.

The particle size obtained measured using Beckman-Coulter LS13320 Laser Diffraction Particle Sizer was d50-153 micrometer.

Example 2

Preparation of Crystalline DMSO Solvate of Prothioconazole

Prothioconazole (Form I or II or a mixture of both) (2 g) in DMSO (8.45 g) was heated in a 250 ml beaker over heating plate until the prothioconazole completely dissolved. The hot solution (at ~75° C.) was kept heated for further 60 minutes, then the heating plate was turned off and the solution allowed to cool on the heating plate to ~35° C. The solution was observed to be cloudy at this temperature. Cyclohexane (9.45 g) was then added drop-wise to the cloudy solution, and after 5 minutes of stirring 3 g of cold water were dropped into the solution, to obtain a slurry. The slurry was immediately cooled to 7° C. in an ice-water bath, stirred for a further 60 minutes and filtered under vacuum. The white crystals obtained from filtration were analyzed by X-ray powder diffraction, IR spectroscopy, and by thermal analysis methods (differential scanning calorimetry (DSC) and thermogravimetric analysis (TGA)).

Figure 2B:
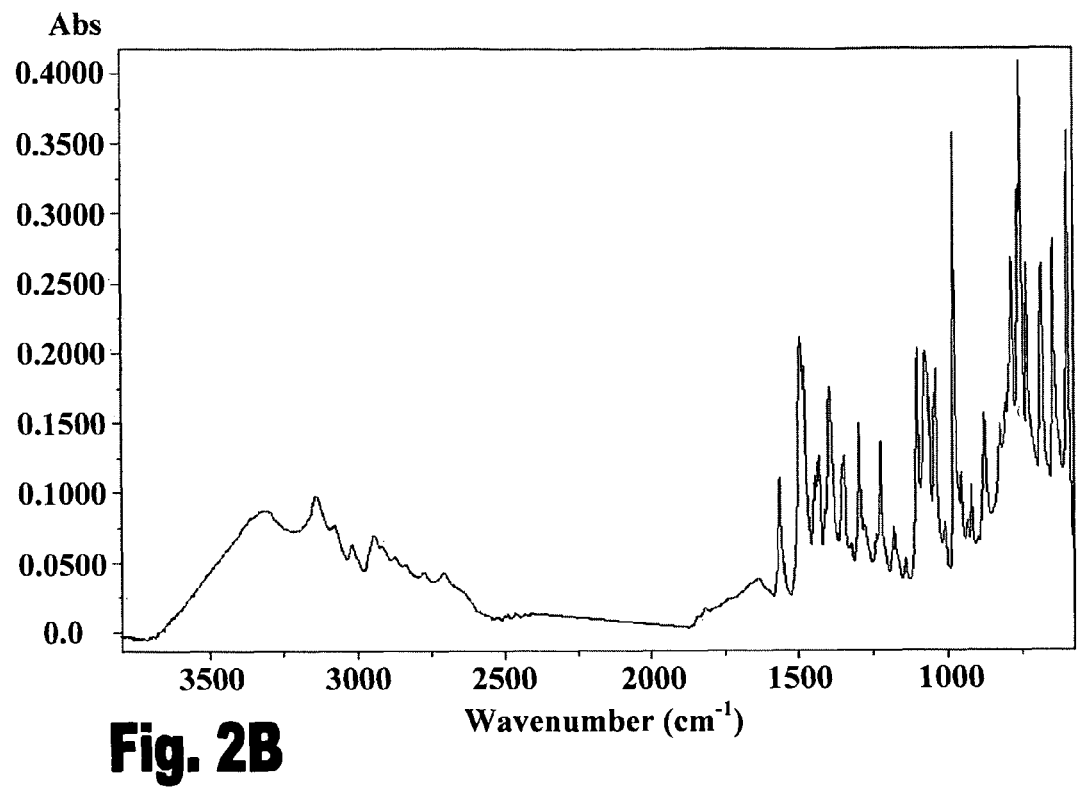
Figure 2C:
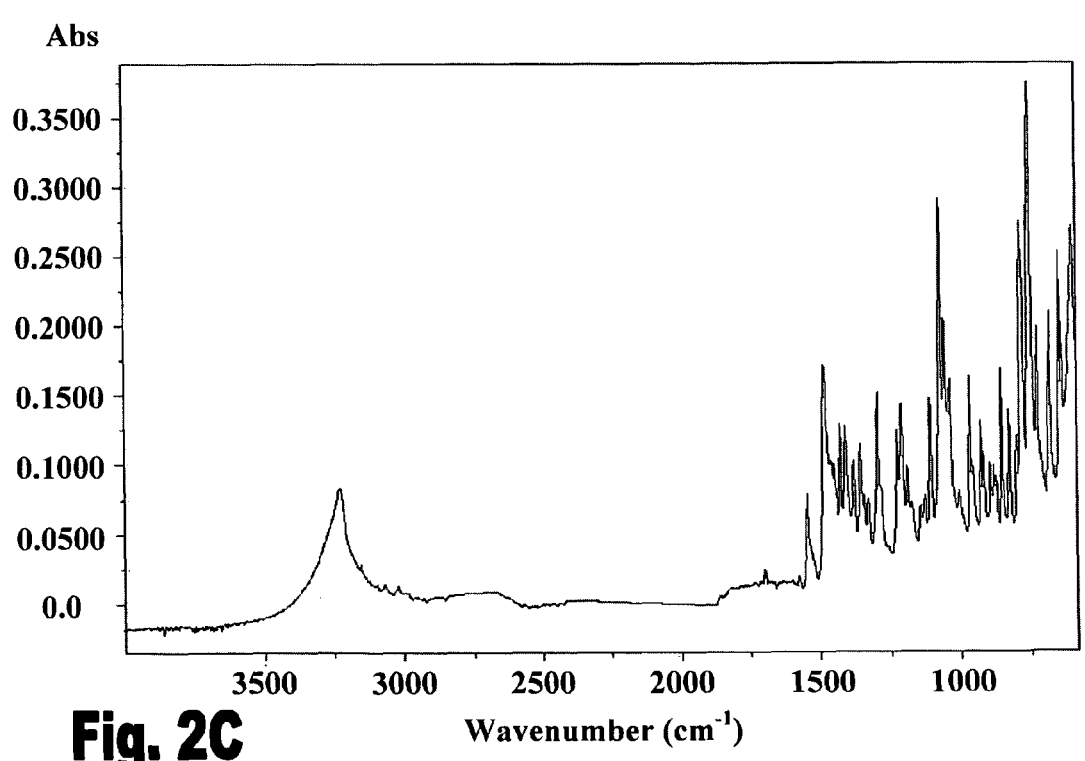

It was determined from TGA, gas chromatography, and gas chromatography-mass spectrometry that the material obtained was a 1:1 prothiaconazole/DMSO solvate. FIGS. 2A, 2B and 2C show FT-IR spectra of crystalline prothiconazole DMSO solvate, crystalline Form I and crystalline Form II prothioconazole, respectively.

Figure 3B:
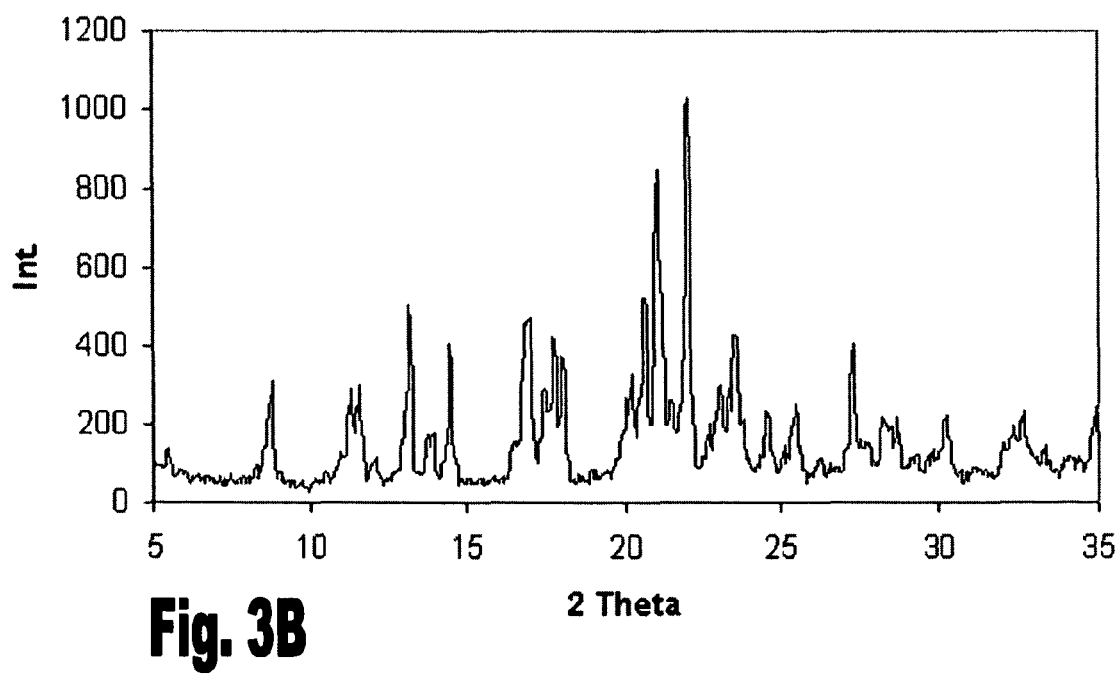
Figure 3C:
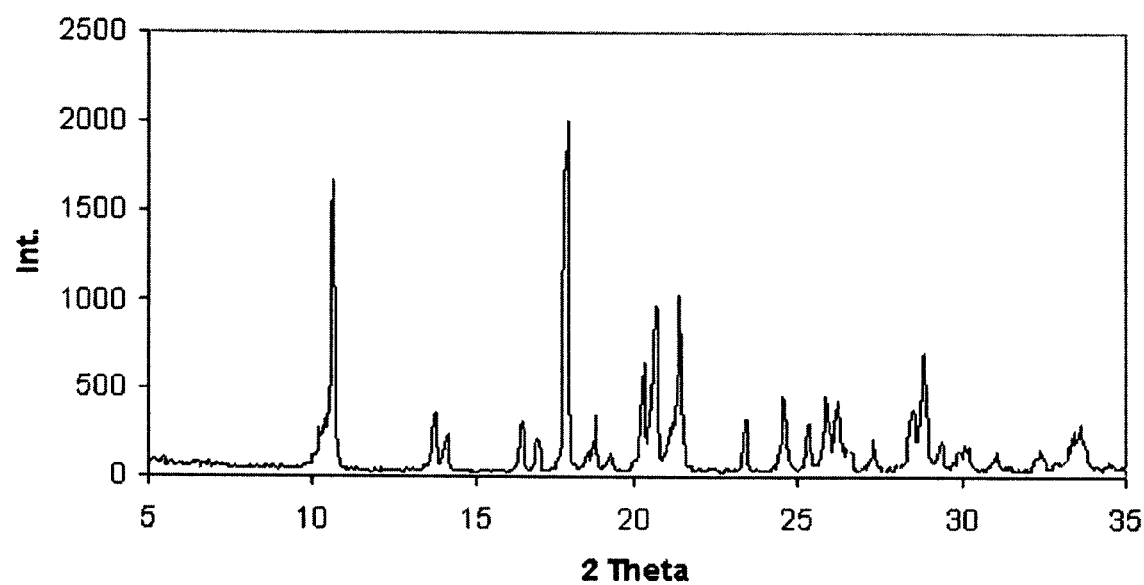

FIGS. 3A, 3B and 3C show respectively XRDs of crystalline prothiconazole DMSO solvate, crystalline Form I and crystalline Form II prothioconazole. FIG. 4A shows in overlayed form DSC plots for crystalline prothioconazole DMSO solvate, crystalline Form I and crystalline Form II prothioconazole. Form I showed an onset temperature of melting of 137.83° C. Form II showed an onset temperature of melting of 138.04° C. The DMSO solvate showed an onset temperature of desolvation of 105.05° C.

FIG. 4B shows a TGA plot for crystalline prothioconazole DMSO solvate. The weight loss was found to be 18.529% which corresponds to the DMSO monosolvate (1:1 prothioconazole/DMSO solvate).

Table 1 presents a partial list of peaks that appear in the FT-IR spectrum of crystalline prothioconazole DMSO solvate.

TABLE 1

| Wavenumber (cm$^{-1}$) ± 0.2 cm$^{-1}$ |
| --- |
| 644.6 |
| 688.8 |
| 712.0 |
| 858.6 |
| 928.1 |
| 1007.0 |
| 1021.0 |
| 1073 |
| 1146.0 |
| 1235.0 |
| 1262 |
| 1304.0 |
| 1320.0 |
| 1401.0 |
| 1549.0 |
| 3259.0 |

Table 2 presents a partial list of 2θ values for peaks in the XRD of crystalline prothioconazole DMSO solvate.

TABLE 2

| 2θ (±0.2 2θ) |
| --- |
| 7.5 (weak) |
| 10.15 (strong) |
| 15.45 (weak) |
| 15.95 |
| 16.75 (medium) |
| 19.40 |
| 21.35 |
| 22.75 (strong) |
| 24.85 (medium) |
| 31.35 (weak) |
| 34.6 (weak) |

Example 3

Solubility of Amorphous Prothioconazole and Prothioconazole DMSO Solvate

The following solubilities were measured in water, 20° C., buffered at pH 7, using the Shake Flask Method (OECD Guideline 105):
Form I: 28 ppm;
Form II: 15 ppm;
Amorphous: 34 ppm;
DMSO Solvate: 30 ppm.

Further runs gave essentially the same values, and in all cases the same order of relative solubility was retained.

The results show a higher solubility for the amorphous prothioconazole and prothioconazole DMSO solvate.

The invention has been described in detail with particular reference to some embodiments thereof, but it will be understood by those skilled in the art that variations and modifications can be effected within the spirit and scope of the invention. It is appreciated that features from different embodiments described in the invention can be combined.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:

1. A method for preparing amorphous prothioconazole, comprising heating crystalline prothioconazole until it melts, and cooling the melted prothioconazole at a rate of 3-20° C./min, to obtain amorphous prothioconazole.

2. A method according to claim 1, wherein said cooling is effected by placing the melted prothioconazole in an environment which is at 25° C. or lower.

3. A method according to claim 1 wherein the amorphous prothioconazole obtained is characterized by a particle size diameter (d50) in the range of 20 to 200 micrometer.

* * * * *